US00RE49978E

(19) United States
(12) Reissued Patent
Lasic et al.

(10) Patent Number: US RE49,978 E
(45) Date of Reissued Patent: May 21, 2024

(54) METHOD OF PERFORMING DIFFUSION WEIGHTED MAGNETIC RESONANCE MEASUREMENTS ON A SAMPLE

(71) Applicant: The Brigham and Women's Hospital, Inc., Boston, MA (US)

(72) Inventors: Samo Lasic, Lund (SE); Daniel Topgaard, Lund (SE); Markus Nilsson, Oxie (SE); Hans Magnus Henrik Lundell, Fredensborg (DK)

(73) Assignee: THE BRIGHAM AND WOMEN'S HOSPITAL, INC., Boston, MA (US)

(21) Appl. No.: 17/555,944

(22) Filed: Dec. 20, 2021

Related U.S. Patent Documents

Reissue of:
(64) Patent No.: 10,948,560
Issued: Mar. 16, 2021
Appl. No.: 16/348,580
PCT Filed: Nov. 9, 2017
PCT No.: PCT/SE2017/051126
§ 371 (c)(1),
(2) Date: May 9, 2019
PCT Pub. No.: WO2018/088955
PCT Pub. Date: May 17, 2018

(30) Foreign Application Priority Data

Nov. 9, 2016 (SE) ..... 1651469-7

(51) Int. Cl.
*G01R 33/563* (2006.01)
*A61B 5/055* (2006.01)
(Continued)

(52) U.S. Cl.
CPC ... *G01R 33/56341* (2013.01); *G01R 33/4835* (2013.01); *G01R 33/543* (2013.01); *G01R 33/5608* (2013.01); *A61B 5/055* (2013.01)

(58) Field of Classification Search
CPC ..... G01R 33/56341; G01R 33/4835; G01R 33/543; G01R 33/5608; A61B 5/055
(Continued)

(56) References Cited

U.S. PATENT DOCUMENTS 5,969,524 A 10/1999 Pierpaoli
6,288,540 B1 9/2001 Chen
(Continued)

FOREIGN PATENT DOCUMENTS

CA 2936624 A1 * 8/2015 ..... A61B 5/055
CN 1653349 A 8/2005
(Continued)

OTHER PUBLICATIONS

Indian Office Action Application No. 201927015276, dated Jun. 21, 2021.
(Continued)

*Primary Examiner* — Kenneth Whittington
(74) *Attorney, Agent, or Firm* — Quarles & Brady LLP

(57) ABSTRACT

According to an aspect of the present inventive concept there is provided a method of performing diffusion weighted magnetic resonance measurements on a sample, the method includes performing diffusion weighted magnetic resonance measurements on the sample, where the measurements include a first measurement with a first diffusion encoding sequence having a first diffusion weighting tensor representation B1 with at least two non-zero eigenvalues and a second measurement with a second diffusion encoding sequence having a second diffusion weighting tensor representation B2 with at least two non-zero eigenvalues. The first tensor representation B1 and the second tensor representation B2 have a same number of non-zero eigenvalues, where the eigenvalues of the first tensor representation B1 matching the eigenvalues of the second tensor representation B2, and the first and the second diffusion encoding
(Continued)

sequences are configured to present a matching average spectral content; and to present a different degree of spectral anisotropy.

16 Claims, 3 Drawing Sheets

(51) Int. Cl.
*G01R 33/483* (2006.01)
*G01R 33/54* (2006.01)
*G01R 33/56* (2006.01)

(58) Field of Classification Search
USPC ..... 324/300–309
See application file for complete search history.

(56) References Cited

U.S. PATENT DOCUMENTS

| | | | | |
|---|---|---|---|---|
| 6,806,705 | B2 | 10/2004 | van Muiswinkel et al. | |
| 7,633,291 | B2 | 12/2009 | Zwanger | |
| 7,906,965 | B2 | 3/2011 | Koay | |
| 8,436,613 | B2 | 5/2013 | Feiweier | |
| 8,508,226 | B2 | 8/2013 | Feiweier et al. | |
| 8,781,197 | B2 | 7/2014 | Wang et al. | |
| 9,233,763 | B1 | 1/2016 | Chen et al. | |
| 9,250,307 | B2 | 2/2016 | Huwer et al. | |
| 9,891,302 | B2 | 2/2018 | Topgaard | |
| 10,684,337 | B2 | 6/2020 | Wu et al. | |
| 11,061,096 | B2 * | 7/2021 | Lasic | G01R 33/4835 |
| 2002/0042569 | A1 | 4/2002 | Wedeen | A61B 5/055 600/416 |
| 2005/0068031 | A1 | 3/2005 | Frank | |
| 2006/0241375 | A1 | 10/2006 | Van Den Brink | |
| 2007/0238969 | A1 | 10/2007 | Song | |
| 2009/0091322 | A1 | 4/2009 | Posse | |
| 2009/0118608 | A1 | 5/2009 | Koay | |
| 2011/0199084 | A1 | 8/2011 | Hasan | |
| 2012/0038673 | A1 | 2/2012 | Iwata | |
| 2015/0115957 | A1 | 4/2015 | Topgaard | |
| 2015/0130458 | A1 | 5/2015 | Topgaard | |
| 2015/0153433 | A1 * | 6/2015 | Paulsen | G01N 24/081 324/309 |
| 2015/0219782 | A1 * | 8/2015 | Kadayam Viswanathan | G01V 3/14 324/309 |
| 2015/0253410 | A1 | 9/2015 | Warfield et al. | |
| 2015/0261808 | A1 * | 9/2015 | Zhou | G06F 16/2358 707/703 |
| 2016/0018504 | A1 | 1/2016 | Magin et al. | |
| 2016/0231410 | A1 * | 8/2016 | Warfield | A61B 5/055 |
| 2016/0356873 | A1 | 12/2016 | Topgaard | |
| 2017/0234956 | A1 | 8/2017 | Feiweier | |
| 2019/0265323 | A1 | 8/2019 | Lasic | |

FOREIGN PATENT DOCUMENTS

| | | | |
|---|---|---|---|
| CN | 1961826 | A | 5/2007 |
| CN | 101143093 | A | 3/2008 |
| CN | 101879063 | A | 11/2010 |
| CN | 102077108 | A | 5/2011 |
| CN | 102144923 | A | 8/2011 |
| CN | 102736046 | A | 10/2012 |
| CN | 105143904 | A | 12/2015 |
| CN | 105980876 | A | 9/2016 |
| EP | 2955536 | A1 | 12/2015 |
| EP | 3081955 | A1 | 10/2016 |
| JP | 2009-524830 | A | 7/2009 |
| JP | 2015-518408 | A | 7/2015 |
| JP | 2015518568 | A | 7/2015 |
| JP | 2017507698 | A | 3/2017 |
| WO | 2010134870 | A1 | 11/2010 |
| WO | 2013165312 | A1 | 11/2013 |
| WO | 2013165313 | A1 | 11/2013 |
| WO | 2013165313 | A2 | 11/2013 |
| WO | 2015042416 | A1 | 3/2015 |
| WO | 2015119569 | A1 | 8/2015 |
| WO | 2017116300 | A1 | 7/2017 |
| WO | 2017190029 | A1 | 11/2017 |

OTHER PUBLICATIONS

Japanese Office Action Application No. 2019-522714, dated Aug. 3, 2021.
Chinese Office Action dated Nov. 30, 2020.
Chinese Office Action dated Sep. 23, 2020.
D. Jones, "Studying connections in the living human brain with diffusion MRI", Cortex, Sep. 1, 2008, vol. 44, nr. 8, pp. 936-952.
W. Zhan, et al., "A rotation-invariant spherical harmonic decomposition method for mapping intravoxel multiple fiber structures", NeuroImage, Feb. 15, 2006, vol. 29, nr. 4, pp. 1212-1223.
A. Alexander et al., "Diffusion Tensor Imaging of the Brain", Neurotherapeutics: The Journal of the American Society for Experimental Neuro Therapeutics, vol. 4, No. 3, Jun. 2007, pp. 316-329.
P. Basser, et al., "Spectral decomposition of a 4th-order covariance tensor: Applications to diffusion tensor MRI", Signal Processing vol. 87, No. 2, Oct. 24, 2006, pp. 220-236.
S. Vos, et al., "The influence of complex white matter architecture on the mean diffusivity in diffusion tensor MRI of the human brain", NeuroImage 59, pp. 2208-2216, Oct. 8, 2011.
S. Jespersen, et al., "The displacement correlation tensor: Microstructure, ensemble anisotropy and curving fibers", Journal of Magnetic Resonance 208, pp. 34-43, Jan. 1, 2011.
Jie Huang, et al "Simultaneous magnetic resonance imaging of diffusion anisotropy and diffusion gradient", Magnetic Resonance Imaging 26 (2008) pp. 337-346.
Partha P. Mitra "Multiple wave-vector extensions of NMR pulsed-field-gradient spin-echo diffusion measurement" Physical Review B, vol. 51, No. 21, Jun. 1, 1995, pp. 74-78.
Janez Stepisnik "Time-dependent self-diffusion by NMR spin-echo" Physica B 183 (1993) 343-350, Received Jul. 23, 1992, revised Nov. 20, 1992.
Bennett A. Landman, et al "Effects of diffusion weighting schemes on the reproducibility of DTI-derived fractional anisotropy, mean diffusivity, and principal eigenvector measurements at 1.5T", NeuroImage, www.elsevier.com/locate/ynimg NeuroImage 36 (2007) 1123-1138, revised Feb. 16, 2007; accepted Feb. 18, 2007, Available online Apr. 4, 2007.
Indian Office Action Application No. 201927016371, dated Jun. 24, 2021.
Japanese Office Action dated Jul. 29, 2021.
Furo et al., NMR Methods Applied to Anisotropic Diffusion, Magnetic Resonance in Chemistry, 40:S3-S14 (Year: 2002).*
International Search Report for PCT/SE2017/051125 dated Mar. 12, 2018, 9 pages.
D. Jones, "Studying connections in the living human brain with diffusion MRI", Cortex, May 23, 2008, vol. 44, nr. 8, pp. 936-952.
W. Zhan, et al., "A rotation-invariant spherical harmonic decomposition method for mapping intravoxel multiple fiber structures", NeuroImage, Oct. 12, 2005, vol. 29, nr. 4, pp. 1212-1223.
D. Topgaard, "Multidimensional diffusion MRI", Physical Chemistry, Journal of Magnetic Resonance 275, Dec. 19, 2016, pp. 98-113.
J. Sjolund, et al., "Constrained optimization of gradient waveforms for generalized diffusion encoding", Journal of Magnetic Resonance 261, Oct. 31, 2015, pp. 157-168.
C. Westin, et al., "Measurement Tensors in Diffusion MRI: Generalizing the Concept of Diffusion Encoding", MICCAI 2014, Part III, LNCS 8675, pp. 209-216, Jan. 2014.
Y. Wu., et al., Age-and gender-related changes in the normal human brain using hybrid diffusion imaging (HYDI), NeuroImage 54, pp. 1840-1853, Oct. 13, 2010.
C. Westin, et al., "Q-space trajectory imaging for multidimensional diffusion MRI ofthe human brain", NeuroImage 135, pp. 345-362, Feb. 23, 2016.

(56) References Cited

OTHER PUBLICATIONS

International Search Report for PCT/SE2017/051126 dated Mar. 12, 2018, 8 pages.
Extended European Search Report dated Jun. 12, 2020
Extended European Search Report dated Jun. 17, 2020.
Mads Bak, et al "Repulsion, A Novel Approach to Efficient Powder Averaging in Solid-State NMR", Journal of Magnetic Resonance 125, 132-139 (1997) Article No. MN961087, Nov. 12, 1996, pp. 1-8.
Stefanie Eriksson, et al "NMR diffusion-encoding with axial symmetry and variable anisotropy: Distinguishing between prolate and oblate microscopic diffusion tensors with unknown orientation distribution" AIP, The Journal of Chemical Physic 142, 104201 (2015), pp. 1-12.
Stefanie Eriksson, et al "Isotropic weighting in PGSE NMR by magic-angle spinning of the q-vector", Journal of Magnetic Resonance 226 (2013, pp. 13-18.
Samo Lasic "Spectral characterization of diffusion with chemical shift resolution: Highly concentrated water-in-oil emulsion" Journal of Magnetic REsonance 199 (2009) pp. 166-172.
Samo Lasic "Microanisotropy imaging: quantification of microscopic diffusion anisotropy and orientational order parameter by diffusion MRI with magic-angle spinning of the q-vector", Frontiers in PHYSICS, published Feb. 27, 2014, vol. 2, article 11, pp. 1-14.
Henrik et al "Spectral anisotropy in multidimensional diffusion encoding" Danish Research Centre for Magnetic Resonance, Proc. Intl. Soc. Mag. Reson, Med. 26 (2018), pp. 1-2.
Henrik Lundell "Microscopic anisotropy with spectrally modulated q-space trajectory encoding", Proc. Intl. Soc. Mag. Reson. Med. 25 (2017). pp. 1-3.
Markus Nilsson "Resolution limit of cylinder diameter estimation by diffusion MRI: The impact of gradient waveform and orientation dispersion", Wiley NMR Inbiomedicine, Jan. 20, 2017, pp. 1-13.
Markus Nilsson, "Estimating the axon diameter from intra-axonal water diffusion with arbitrary gradient waveforms: Resolution limit in parallel and dispersed fibers", Proc. Intl. Soc. Mag. Reson. Med. 24 (2016), pp. 1-4.
Noam Shemesh "Conventions and Nomenclature for Double Diffusion Encoding NMR and MRI" Magnetic Resonance in Medicine 75:82-87 (2016), pp. 82-87.
J. Stepisnik "Analysis of NMR Self-Diffusion Measurements by a Density Matrix Calculation" Physica 104B (1981) 350-364, Nov. 21, 1979, revised Jul. 24, 1980.
Janez Stepisnik "Validity limits of Gaussian approximation in cumulant expansion for diffusion attenuation of spin echo", Physica B 270 (1999), 110-117, pp. 1-8, Dec. 5, 1997, revised Dec. 17, 1998.
Filip Szczepankiewicz "Quantification of microscopic diffusion anisotropy disentangles effects of orientation dispersion from microstructure: Applications in healthy volunteers and in brain tumors", NeuroImage 104 (2015) 241-252.
J. E. Tanner "Restricted Self-diffusion of Protons in Colloidal Systems by the Pulsed-Gradient, Spin-Echo Method", The Journal of Chemical Physics, vol. 49, No. 4, Aug. 15, 1996, pp. 1-10.
Daniel Topgaard "Isotropic diffusion weighting in PGSE NMR: Numerical optimization of the q-MAS PGSE sequence" Microporous and Mesoporous Materials 178 (2013) 60-63.
D.E. Woessner "N.M.R. Spin-Echo Self-diffusion measurements on fluids undergoing restricted diffusion", Socony Mobil Oil Company, Inc., Field Research Laboratory, Dallas, Texas, Jun. 1963, pp. 1-3.

* cited by examiner

METHOD OF PERFORMING DIFFUSION WEIGHTED MAGNETIC RESONANCE MEASUREMENTS ON A SAMPLE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This Application is the National Stage filing under 35 U.S.C. § 371 of PCT Application Ser. No. PCT/SE2017/051126 filed on Nov. 9, 2017, which claims the benefit of Sweden Patent Application No. 1651469-7 filed on Nov. 9, 2016. The disclosures of both applications are hereby incorporated herein by reference in their entireties.

TECHNICAL FIELD

The present inventive concept relates to a method of performing diffusion weighted magnetic resonance measurements on a sample.

BACKGROUND

In magnetic resonance (MR) or magnetic resonance imaging (MRI) experiments, information about motion or diffusion of particles can be encoded by applying motion or diffusion encoding magnetic field gradient.

Motion or diffusion encoded signals can be used to infer information about tissue microstructure, anisotropy, shape and size of the constituent compartments, which may represent confinements/restrictions for diffusion of spin-bearing particles. The fractional anisotropy (FA) obtained by diffusion tensor imaging (DTI) is confounded by compartmental macroscopic orientation dispersion. To separate the effects of orientation dispersion from the anisotropy of diffusion tensors, which may represent confinements, and are entangled in the FA, the directional diffusion encoding (1D) needs to be combined or substituted with encoding schemes extending beyond a single direction (to 2D or 3D). These schemes can be described by diffusion encoding/weighting tensors with more than one non-zero eigenvalues (1) and can, to various degrees, reduce or eliminate the confounding effect of orientation dispersion and provide sensitivity specific to compartment (diffusion tensor) anisotropy.

The approach by Lasič et al. (2), which maximizes the sensitivity to compartment (diffusion tensor) anisotropy, combines directional (1D) and isotropic (3D) encoding to quantify microscopic fractional anisotropy (μFA). The isotropic encoding can, for example, be achieved by the magic angle spinning of the q-vector (qMAS) (3), while the diffusion weighting for the directional encoding is matched to that of the qMAS in terms of diffusion time, $t_d$, and b-value. Oblate and prolate compartment (diffusion tensor) shapes can be distinguished by further controlling the anisotropy of the diffusion encoding. Eriksson et al. (4) have shown that by parameterizing the diffusion encoding tensor in terms of its size and shape, a simple expression for the powder average signal is obtained, allowing to quantify compartment (diffusion tensor) shapes. Varying the diffusion encoding shape is necessary for systems with a non-zero dispersion of isotropic diffusivities (2). Using 3D encoding sequences allows to de-convolve the anisotropic and isotropic diffusion contributions (5).

Despite the above-mentioned advances in characterizing heterogeneous and anisotropic materials, it would be desirable to be able to extract even further information relating to the diffusion characteristics and the microscopic structures of samples.

SUMMARY OF THE INVENTIVE CONCEPT

An objective of the present inventive concept is to provide a method enabling extracting of further information relating to the diffusion characteristics and the microscopic structures of a sample. Further or alternative objectives may be understood from the following.

According to an aspect of the present inventive concept there is provided a method of performing diffusion weighted magnetic resonance measurements on a sample, the method comprising:

performing diffusion weighted magnetic resonance measurements on the sample, wherein said measurements includes:

a first measurement with a first diffusion encoding sequence having a first diffusion weighting tensor representation $B_1$ with at least two non-zero eigenvalues, a second measurement with a second diffusion encoding sequence having a second diffusion weighting tensor representation $B_z$ with at least two non-zero eigenvalues, wherein the first tensor representation $B_1$ and the second tensor representation $B_z$ have a same number of non-zero eigenvalues, the eigenvalues of the first tensor representation $B_1$ matching the eigenvalues of the second tensor representation $B_z$, and wherein the first and the second diffusion encoding sequences are configured to present a matching average spectral content, and to present a different degree of spectral anisotropy.

The present inventive concept is based on the following insights: While diffusion tensors may roughly represent physical pores, a more accurate detection of morphology can be achieved by varying the spectral characteristics (equivalently temporal characteristics) of encoding waveforms, thus probing time-dependent non-Gaussian diffusion. The spectral characteristics of a diffusion encoding sequence waveform include an average spectral content of each spatial channel of the encoding waveform. An "average spectral content" of a diffusion encoding sequence may hence notionally be referred to as a "color" of the encoding waveform. This is reminiscent of an average or mixture of different spectral components of visible light producing a perceived color. In addition to "color" the temporal characteristics of a diffusion encoding sequence waveform include a degree of spectral anisotropy. A "degree of spectral anisotropy" may notionally be thought of as a property which is dependent on how spectrally different the spatial channels of the encoding waveform are.

By the first and the second diffusion encoding sequences presenting matching spectral content but different degrees of spectral anisotropy, the combination of measurements on the sample is configured to be sensitive to restricted diffusion from anisotropic diffusion structures. Hence, a contribution to a resulting signal attenuation from isotropic diffusion structures presenting restricted diffusion may be minimized or at least reduced.

By "diffusion" as used herein, is herein meant a random or stochastic process of motion of particles within the sample. Diffusion may include random molecular motion driven by thermal energy, chemical energy and/or concentration difference. Diffusion may include dispersed or incoherent flow of molecules (i.e. flow with velocity dispersion) inside randomly oriented microstructures within the sample. Due to the diffusion encoding magnetic field gradient sequences used in the present method the effects of incoherent flow within the sample may also give rise to signal attenuation.

The diffusion characteristics of a sample (i.e. the degree of isotropic diffusion, the degree and/or orientation of the anisotropic diffusion etc.) generally depend on the geometries and orientations of the diffusion restricting structures in the sample. Partial volumes of a sample having presenting different diffusion characteristics may be referred to as different compartments of the sample. A diffusion weighted measurement signal from a voxel of the sample (i.e. a partial volume of the sample with a dimension given by the spatial resolution of the measurement) hence includes signal contributions from diffusing particles inside the different compartments within the voxel.

In the prior art, analysis of compartment anisotropy based on diffusion weighted magnetic resonance measurements assumes that the diffusion process is Gaussian or multi-Gaussian. This assumption is equivalent to assuming that the diffusion process is time-independent (or equivalently frequency-independent). However, as realized by the inventors, the presence of physical restrictions for the diffusion particles may be manifested by a frequency dependent signal attenuation.

A diffusion process may in a frequency domain be described by a diffusion spectrum, i.e. a spectrum of correlations of the velocities of the moving particles. The measurement protocol in accordance with the inventive method includes the first and second encoding sequences with purposefully selected spectral characteristics, i.e. matching average spectral content and different degrees of spectral anisotropy. Comparison of signal attenuations from the first and second measurement thereby enables probing of the diffusion spectrum, i.e. the frequency dependence of a diffusion characteristics of the sample. The present method allows probing of the diffusion spectrum or provides sensitivity to different spectral components of the diffusion spectrum in the range of frequencies that can be detected with conventional hardware for magnetic resonance measurements (typically below 1 Gigahertz).

In a tissue sample, compartments may be formed by cells in the tissue. Hence, a voxel in a tissue sample may include a signal contribution from diffusion inside a cell (i.e. from an intracellular compartment) and a signal contribution from diffusion outside a cell (i.e. from an extracellular compartment). The diffusing spin-bearing particles may be formed by water molecules inside and outside the cells. The cell membranes may form compartment walls separating the intracellular and extracellular compartment.

As may be understood from the following, the diffusion encoding sequences referred to in the above method aspect may refer to the effective gradient sequences, i.e. the effective magnetic field gradient experienced by the spin bearing particles in the sample due to a combination of a magnetic field gradient sequence and a radio frequency (RF) sequence. Hence, unless stated otherwise, the term diffusion encoding sequence refers to an encoding sequence including a magnetic field gradient sequence and an RF sequence adapted to cause diffusion encoding/weighting (i.e. of an echo signal attenuation).

A diffusion encoding may be achieved by subjecting the sample to encoding magnetic field gradient waveforms and a sequence of RF pulses. The combined effect of magnetic field gradient waveforms and RF pulses results in (the spin bearing particles in) the sample being subjected to an "effective gradient". The waveform of the effective gradient may be referred to as the effective gradient waveform g(t) with components NO, where i=1, 2, 3 representing e.g. x, y, z axis in the Cartesian coordinate system.

The effective gradient may be represented by the time-dependent or temporal dephasing vector F(t), with components $F_1$, where i=1, 2, 3, which in turn is given by $$F(t)=\gamma\int_0^t g(t')dt', \tag{1}$$

where γ is where the nuclear gyromagnetic ratio.

A dephasing spectrum, i.e. a spectral content of the dephasing vector is given by:

$$F(\omega)=\int_0^\tau F(t)e^{-i\omega t}dt, \tag{2}$$

where ω denotes frequency and τ denotes the diffusion encoding time, i.e. the duration of the effective gradient.

Based on the dephasing spectrum F(ω), the moments of dephasing spectra may be defined as $$M_{ij}^{(n)}=\int_{-\infty}^{\infty}F_1(\omega)F_j^*(\omega)|\omega|^n d\omega, \tag{3}$$

represented as a tenor $M^{(n)}$, where $M_{ij}^{(n)}$ are the tensor elements. The $0^{th}$ moment, $M^{(0)}$, gives the diffusion weighting tensor B. For Gaussian diffusion, only $B_{1j}=M_{ij}^{(0)}$ needs to be considered.

Accordingly, the diffusion weighting tensor representation B of a diffusion encoding magnetic gradient sequence is given by $$B=\int_{-\infty}^{\infty}F(\omega)F^*(\omega)d\omega \tag{4}$$

The dephasing vector F(t) may also be expressed as the Hadamard product of the amplitude q of the dephasing vector and the normalized dephasing vector waveform $\tilde{F}(t)$, $$F(t)=q\circ\tilde{F}(t). \tag{5}$$

The dephasing spectra may accordingly also/alternatively be given by $$F(\omega)=q\circ\int_0^\tau\tilde{F}(t)e^{-i\omega t}dt=q\circ\tilde{F}(\omega), \tag{6}$$

where $\tilde{F}(\omega)$ may be referred to as the normalized dephasing spectra, i.e. the spectral content of the normalized dephasing vector. The spectra $F_1(\omega)$ and $\tilde{F}_i(\omega)$, where i=1, 2, 3 representing e.g. x, y, z axis in the Cartesian coordinate system, may be referred as the orthogonal components or projections of the spectral representation of the dephasing vector or the normalized dephasing vector, respectively.

In terms of the normalized spectra $\tilde{F}(\omega)$ in Eq. (6), the elements of the tensor $M^{(n)}$ are given by:

$$M_{ij}^{(n)}=q_iq_j\int_{-\infty}^{\infty}\tilde{F}_i(\omega)\tilde{F}_j^*(\omega)|\omega|^n d\omega=Q_{ij}m_{ij}^{(n)}. \tag{7}$$

The term $m_{ij}^{(0)}$ corresponds to a generalized diffusion time. Expressed in matrix form; $M^{(n)}=Q\circ m^{(n)}$ and $t_d=m^{(0)}$.

In 1D encoding, the dephasing waveform may be constructed from the dephasing magnitude of a 3D encoding, so that the 1D encoding matches the 3D encoding in terms of the diffusion time, e.g. so that the square of 1D dephasing amplitude is given by the sum of squared dephasing amplitude components of a 3D encoding, $\tilde{F}(t)^2=\Sigma_i\tilde{F}_i(t)^2$.

The diffusion spectrum D(ω) may be defined as the spectrum of the velocity correlation tensor, $\chi(t)=\langle v^T(t)v(0)\rangle$.

In the principal axis system of the compartments, $D(\omega)$ is diagonal, given by diffusion spectra $\lambda_i(\omega)$ along the diagonal of matrix $\lambda(\omega)$. The elements $\lambda_i(\omega)$ may be referred to as the diffusion tensor eigenvalues.

The apparent diffusivities are then given by $$\Lambda_{ijk} \equiv \frac{\int_{-\infty}^{\infty} F_i(\omega)\lambda_k(\omega)F_j^*(\omega)d\omega}{\int_{-\infty}^{\infty} F_i(\omega)F_j^*(\omega)d\omega}. \tag{8}$$

As may be understood from the above, a spectral content of an (effective) diffusion encoding magnetic gradient sequence or, equivalently, the dephasing vector waveform is given by the dephasing spectra $F(\omega)$ or its normalized counterpart $\tilde{F}(\omega)$.

The components of the normalized power spectra are given by:

$$S_{ij}(\omega)=\tilde{F}_i(\omega)\tilde{F}_j^*(\omega) \tag{9}$$

The $n^{th}$ moment of the normalized power spectra may be expressed in a tensor or matrix form $m^{(n)}$, where $$m_{ij}^{(n)} = \int_{-\infty}^{\infty} S_{ij}(\omega)|\omega|^n d\omega = \begin{cases} 0 \text{ if } M_{ij}^{(0)} = 0 \\ \frac{M_{ij}^{(n)}}{M_{ij}^{(0)}} \text{ if } M_{ij}^{(0)} > 0 \end{cases}. \tag{10}$$

where $m_{ij}^{(n)}$ denotes the elements of $m^{(n)}$. With $\mu_i^{(n)}$ we denote the eigenvalues of $m^{(n)}$.

The tensor elements of the tensor $M^{(n)}$ may be given by:

$$M_{ij}^{(n)}=q_iq_j\int_{-\infty}^{\infty}S_{ij}|\omega|^n d\omega \tag{11}$$

Accordingly, the elements of the diffusion weighting tensor B may be given by:

$$B_{ij}=q_iq_j\int_{-\infty}^{\infty}S_{ij}d\omega. \tag{12}$$

The average encoding spectral content (for a single multi-dimensional encoding scheme) can be characterized by $$\langle\mu^n\rangle = \frac{\mu_1^{(n)} + \mu_2^{(n)} + \mu_3^{(n)}}{\mu_1^{(0)} + \mu_2^{(0)} + \mu_3^{(0)}}, \tag{13}$$

where n is any positive real number, $n>0 \wedge n\in\mathbb{R}$. With brackets $\langle \ldots \rangle$ we are denoting the averaging operation. The difference of $\langle\mu^{(n)}\langle$ for any $n>0$ can be used to compare two encoding schemes. Spectral matching or spectral tuning of different diffusion encoding sequences (or equivalently different normalized dephasing vector representations) may refer to having matching $\langle\mu^{(n)}\rangle$. Inversely, different encoding sequences could be considered detuned if their spectral content is not matching, i.e. if $\langle\mu^{(n)}\rangle$ are different.

The spectral anisotropy of diffusion encoding (for a single multidimensional encoding scheme) can be quantified by comparing different eigenvalues of $m^{(n)}$, i.e. the values $\mu_i^{(n)}$. Any measure of tensor anisotropy, e.g. fractional anisotropy, can be applied to the tensors $m^{(n)}$. To quantify spectral anisotropy (SA), the following equation, analogous to the fractional anisotropy, may be used (provided the diffusion encoding tensor representations of the diffusion encoding sequences have more than one non-zero eigenvalue):

$$SA^{(n)} = \left[\frac{1}{2}\frac{\mu_1^{(0)}\mu_2^{(0)}\left(\mu_1^{(n)}-\mu_2^{(n)}\right)^2+\mu_2^{(0)}\mu_3^{(0)}\left(\mu_2^{(n)}-\mu_3^{(n)}\right)^2+\mu_3^{(0)}\mu_1^{(0)}\left(\mu_3^{(n)}-\mu_1^{(n)}\right)^2}{\mu_1^{(n)^2}+\mu_2^{(n)^2}+\mu_3^{(n)^2}}\right]^{1/2}, \tag{14}$$

where n is any positive real number, $n>0 \wedge n\in\mathbb{R}$, which can be adjusted to control the sensitivity to spectral anisotropy. Note that $SA^{(n)}$ is always in the range 0-1. Note that also other quantitative measures of spectral anisotropy may be used, which is applicable to quantification of tensor anisotropy.

In view of the above, the first and the second diffusion encoding sequences may, in accordance with one embodiment, present matching average spectral content in the sense that $\langle\mu^{(n)}\rangle$ calculated for the first diffusion encoding sequence matches $\langle\mu^{(n)}\rangle$ calculated for the second diffusion encoding sequence, for any $n>0$, preferably at least for $n=2$.

Further in view of the above, the first and the second diffusion encoding sequences may, in accordance with one embodiment, present a different degree of spectral anisotropy in the sense that $SA^{(n)}$ calculated for the first diffusion encoding sequence differs from $SA^{(n)}$ calculated for the second diffusion encoding sequence.

Hence, for the first diffusion encoding gradient sequence, $$\langle\mu^{(n)}\rangle = \frac{\mu_1^{(n)} + \mu_2^{(n)} + \mu_3^{(n)}}{\mu_1^{(0)} + \mu_2^{(0)} + \mu_3^{(0)}}, \text{ and}$$

$$SA^{(n)} = \left[\frac{1}{2}\frac{\mu_1^{(0)}\mu_2^{(0)}\left(\mu_1^{(n)}-\mu_2^{(n)}\right)^2+\mu_2^{(0)}\mu_3^{(0)}\left(\mu_2^{(n)}-\mu_3^{(n)}\right)^2+\mu_3^{(0)}\mu_1^{(0)}\left(\mu_3^{(n)}-\mu_1^{(n)}\right)^2}{\mu_1^{(n)^2}+\mu_2^{(n)^2}+\mu_3^{(n)^2}}\right]^{1/2}$$

where $\mu_i^{(n)}$ denotes the eigenvalues of the tensor $m^{(n)}$ with elements $m_{ij}^{(n)}=\int_{-\infty}^{\infty}\tilde{F}_i(\omega)\tilde{F}_j^*(\omega)|\omega|^n d\omega$, where $\tilde{F}_i(\omega)$ and $\tilde{F}_j^*(\omega)$ are the $i^{th}$ and $j^{th}$ components of the normalized dephasing vector, respectively, of the normalized dephasing spectrum $\tilde{F}(\omega)$ representation of the first diffusion encoding gradient sequence.

Moreover, for the second diffusion encoding gradient sequence, $$\langle\mu^{(n)}\rangle = \frac{\mu_1^{(n)} + \mu_2^{(n)} + \mu_3^{(n)}}{\mu_1^{(0)} + \mu_2^{(0)} + \mu_3^{(0)}}, \text{ and}$$

$$SA^{(n)} = \left[\frac{1}{2}\frac{\mu_1^{(0)}\mu_2^{(0)}\left(\mu_1^{(n)}-\mu_2^{(n)}\right)^2+\mu_2^{(0)}\mu_3^{(0)}\left(\mu_2^{(n)}-\mu_3^{(n)}\right)^2+\mu_3^{(0)}\mu_1^{(0)}\left(\mu_3^{(n)}-\mu_1^{(n)}\right)^2}{\mu_1^{(n)^2}+\mu_2^{(n)^2}+\mu_3^{(n)^2}}\right]^{1/2}$$

where $\mu_i^{(n)}$ denotes the eigenvalues of the tensor $m^{(n)}$ with elements $m_{ij}^{(n)}=\int_{-\infty}^{\infty}\tilde{F}_i(\omega)\tilde{F}_j^*(\omega)|\omega|^n d\omega$, where $\tilde{F}_i(\omega)$ and $\tilde{F}_j^*(\omega)$ are the $i^{th}$ and $j^{th}$ eigenvector, respectively, of the normalized dephasing spectrum $\tilde{F}(\omega)$ representation of the second diffusion encoding gradient sequence.

The concept of matching or different "spectral content" may be also be understood from considering a measurement "I" on a "first test sample" with a diffusion encoding sequence "A" and another measurement "II" on the first test sample with a diffusion encoding sequence "B". The first test sample is a sample consisting of a collection of hollow spherical compartments of a 5 μm diameter.

The sequence "A" and the sequence "B" are such that traces of the tensor representations $B_A$, $B_B$ of the sequences "A" and "B" are equal to each other (i.e. they result in a same diffusion encoding strength) and have identical eigenvalues. As the compartments are spherical, the principal axis system and the eigenvectors are degenerate. Hence the tensor representations $B_A$, $B_B$ for sequence "A" and "B" may be given with respect to a three-dimensional Cartesian coordinate system (x,y,x) with an arbitrary orientation with respect to the compartments.

If the sequence "A" and the sequence "B" results in a same level of signal attenuation when applied to the test sample, the sequences are "spectrally matching", i.e. they have matching average spectral content.

If on the other hand the sequence "A" and the sequence "B" results in different levels of signal attenuation when applied to the test sample, the sequences are "spectrally detuned", i.e. they have different average spectral content.

The concept of matching or different "degree of spectral anisotropy" may in a corresponding manner be understood from a measurement "μI" on a "second test sample" with the above-defined diffusion encoding sequence "A" and another measurement "IV" on the second test sample with the above-defined diffusion encoding sequence "B". The second test sample is a sample consisting of a collection of hollow circular cylindrical compartments of a 5 μm diameter with a uniform orientation dispersion. "Uniform orientation dispersion" should here be understood as the orientations of the cylindrical compartments being uniformly distributed over the unit sphere surface.

Assuming that the sequences "A" and "B" are spectrally matching, if the sequence "A" and the sequence "B" results in a same level of signal attenuation when applied to the test sample, the sequences present a same degree of spectral anisotropy. On the other hand, if the sequence "A" and the sequence "B" results in a different level of signal attenuation when applied to the test sample, the sequences present a different degree of spectral anisotropy.

In view of the above, according to one embodiment, the first and the second diffusion encoding sequences are configured such that had:

a third diffusion encoding sequence having a normalized dephasing vector representation $\tilde{F}_3$ matching a first normalized dephasing vector representation $\tilde{F}_1$ of the first diffusion encoding sequence and having a non-zero diffusion encoding strength, been applied to a first test sample consisting of a collection of spherical compartments of a 5 μm diameter, and a fourth diffusion encoding sequence having a normalized dephasing vector representation $\tilde{F}_4$ matching a second normalized dephasing vector representation $\tilde{F}_2$ of the second diffusion encoding sequence and having said non-zero diffusion encoding strength, been applied to said first test sample;

a signal attenuation resulting from the third diffusion encoding sequence would match a signal attenuation resulting from the fourth diffusion encoding sequence;

and such that had:

the third diffusion encoding sequence been applied to a second test sample consisting of a collection of cylindrical compartments of a 5 μm diameter with a uniform orientation dispersion, and the fourth diffusion encoding sequence been applied to said second test sample;

a signal attenuation resulting from the third diffusion encoding sequence would differ from a signal attenuation resulting from the fourth diffusion encoding sequence.

The wording "configured such that had a third/fourth diffusion encoding sequence . . . been applied to the test sample" should hereby not be construed as a sequence of steps which necessarily are required to actively be performed in the claimed method. Rather, the wording should be understood as a functional definition of the properties of the first and second diffusion encoding sequences. Hence, on a condition that/if the third and fourth diffusion encoding sequences had been/would be applied to the test sample the stated signal attenuations would entail. The functional definition may be understood as a clear and well-defined test case for a skilled person to determine whether a set of diffusion encoding sequences have the inventive properties. Indeed, it would not even be necessary to perform an actual measurement on a real "test sample" to test the properties. Rather the test case could be evaluated by measuring a respective RF sequence and magnetic field gradient sequence of a first and second diffusion encoding sequences and from the measurements calculating the tensor representations and normalized dephasing vector representations of the first and second diffusion encoding sequences, and then simulate (by numerical calculations or Monte Carlo simulations) the resulting signal attenuations if a third and fourth diffusion encoding sequence (having the above stated encoding strengths and normalized dephasing vector representations) had been applied to the first and second test objects.

In the above and in the following, it is stated that two or more quantities (e.g. two more diffusion encoding strengths, traces, eigenvalues, $\langle \mu^{(n)} \rangle$ or $SA^{(n)}$) matching each other. "Matching" may in such a context be understood as the quantities being equal, or at least substantially equal. I.e. the quantities need not be exactly equal, but the quantities should differ only by an amount such that the effects of compartment anisotropy, spectral content and spectral anisotropy are possible to discern from the measurements. Preferably the quantities should differ by 10% or less, more preferably by 5% or less, and even more preferably by 1% or less. A may be understood, the maximum achievable level of equality may in practice inter alia depend on the performance of the equipment.

A "diffusion encoding strength" of a diffusion encoding sequence, as used herein, refers to the b-value which is given by the trace of the diffusion encoding tensor for the diffusion encoding sequence.

In accordance with the present method, diffusion weighted magnetic resonance measurements are performed. The measurements includes at least two measurements (i.e. the "first" and "second") each measurement including subjecting the sample to a diffusion encoding sequence. As used herein, the labels "first" and "second" of the measurements/encoding sequences do not imply that the measurements are performed in that particular order but may be performed in any order.

Each one of said diffusion weighted magnetic resonance measurements may generally include an encoding block and a subsequent detection block. During the encoding block, the sample is subjected to a diffusion encoding sequence. During the detection block a signal, attenuated due to diffusion encoding, may be detected and acquired. The detected signal or measurement signal may be an attenuated echo signal.

The encoding block may further include a radio frequency (RF) pulse sequence adapted to influence the magnetization within the sample. The RF pulse sequence may encode for attenuation due to only longitudinal, only transverse relaxation or both longitudinal and transverse relaxation. Hence the attenuation of the signal detected in the detection block is the result of attenuation due to both the diffusion encoding magnetic gradient pulse sequence and the RF pulse sequence, i.e. the attenuation due to the effective gradient sequence g(t) or the corresponding the dephasing vector F(t).

Preferably, said plurality of measurements are performed with the same RF pulse sequence with identical timing. That is the same level of signal attenuation due to nuclear relaxation is encoded for in each measurement. This may simplify data analysis since the number of varying parameters influencing the measurement may be reduced.

For the purpose of acquiring the (attenuated) measurement signals, each diffusion encoding sequence may be supplemented with one or more imaging magnetic gradients and optionally magnetic gradient correction gradients, as is well-known in the art. An imaging magnetic gradient sequence and a correction magnetic gradient sequence may be applied to the sample during the encoding block. In some cases, these sequences may overlap the diffusion encoding magnetic gradient pulse sequence, at least partly. However even in such a case, at least a part of the combined gradient pulse sequence includes a diffusion encoding sequence which may be described or characterized as set out above.

According to one embodiment, said first measurement includes acquiring a first signal attenuation resulting from said first diffusion encoding sequence, and said second of measurements includes acquiring a second signal attenuation resulting from said second diffusion encoding sequence.

According to one embodiment said measurements includes:

a first set of measurements including said first measurement and a plurality of additional measurements performed with said first diffusion encoding sequence applied to the sample with different rotations with respect to a measurement frame of reference, a second set of measurements including said second measurement and a plurality of additional measurements performed with said second diffusion encoding sequence applied to the sample with different rotations with respect to the measurement frame of reference.

This enables determining of directionally averaged signal attenuations (also known as "powder averaging").

Hence, according to one embodiment:

each measurement of said first set of measurements includes acquiring a respective signal attenuation resulting from said diffusion encoding sequence and the method comprises determining a first average signal attenuation based on said respective signal attenuations, and each measurement of said second set of measurements includes acquiring a respective signal attenuation resulting from said diffusion encoding sequence and the method comprises determining a second average signal attenuation based on said respective signal attenuations.

According to one embodiment the method further comprises: generating an output indicative of a difference between the first and second signal attenuations or between the first and second average signal attenuations. The output may hence be sensitive to time-dependent anisotropic diffusion, i.e. signal attenuation due to time-dependent diffusion in anisotropic domains.

According to one embodiment, said first tensor representation has three matching non-zero eigenvalues.

According to one embodiment, said second tensor representation has three matching non-zero eigenvalues.

According to one embodiment, said first tensor representation has exactly two matching non-zero eigenvalues.

According to one embodiment, said second tensor representation has exactly two matching non-zero eigenvalues.

According to one embodiment, performing said measurements includes, measuring a respective signal attenuation resulting from each one of said measurements, from each one of a plurality of voxels within a region of interest of the sample.

According to one embodiment, the method further comprises generating an output including an indication of voxels for which a signal attenuation acquired in the first measurement differs from a signal attenuation acquired in the second measurement.

According to a second aspect of the present inventive concept there is provided method of performing diffusion weighted magnetic resonance measurements on a sample, the method comprising:

performing diffusion weighted magnetic resonance measurements on the sample, wherein said measurements includes:

a first set of measurement performed with diffusion encoding sequences with different diffusion encoding strengths and matching average spectral content and matching degree of spectral anisotropy, a second set of measurement performed with diffusion encoding sequences with different diffusion encoding strengths and matching average spectral content and matching degree of spectral anisotropy, wherein the degree of spectral anisotropy of the diffusion encoding sequences of the first set differs from the degree of spectral aniostropy of the diffusion encoding sequences of the second set.

The advantages and detailed described in connection with the first aspect applies correspondingly to the second aspect.

The above mathematical and test-based definitions of matching average spectral content and matching degree of spectral anisotropy applies correspondingly to each one of the encoding sequences of the first and the second set.

According to one embodiment the method further comprises:

fitting by a first function to a first data set representing said first set of measurements to estimate a first signal attenuation curve, and fitting a second function to a second data set representing said second set of measurements to estimate a second signal attenuation curve.

By estimating a respective signal attenuation curve corresponding each of the first and second sets of measurements further analysis of diffusion characteristics and frequency dependence thereof is enabled. A same fitting function may be used for fitting to the first and the second data set.

According to one embodiment the method further comprises generating an output based on at least one parameter of the first function, at least one parameter of the second function and at least one parameter of the third function.

According to one embodiment the diffusion encoding sequences of each one of the first set and the second set have a respective tensor representation, wherein the number of non-zero eigenvalues of the tensor representations are equal.

According to one embodiment the average spectral content of each of the diffusion encoding sequences of the first set matches the average spectral content of each of the diffusion encoding sequences of the second set.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION

Figure 1:
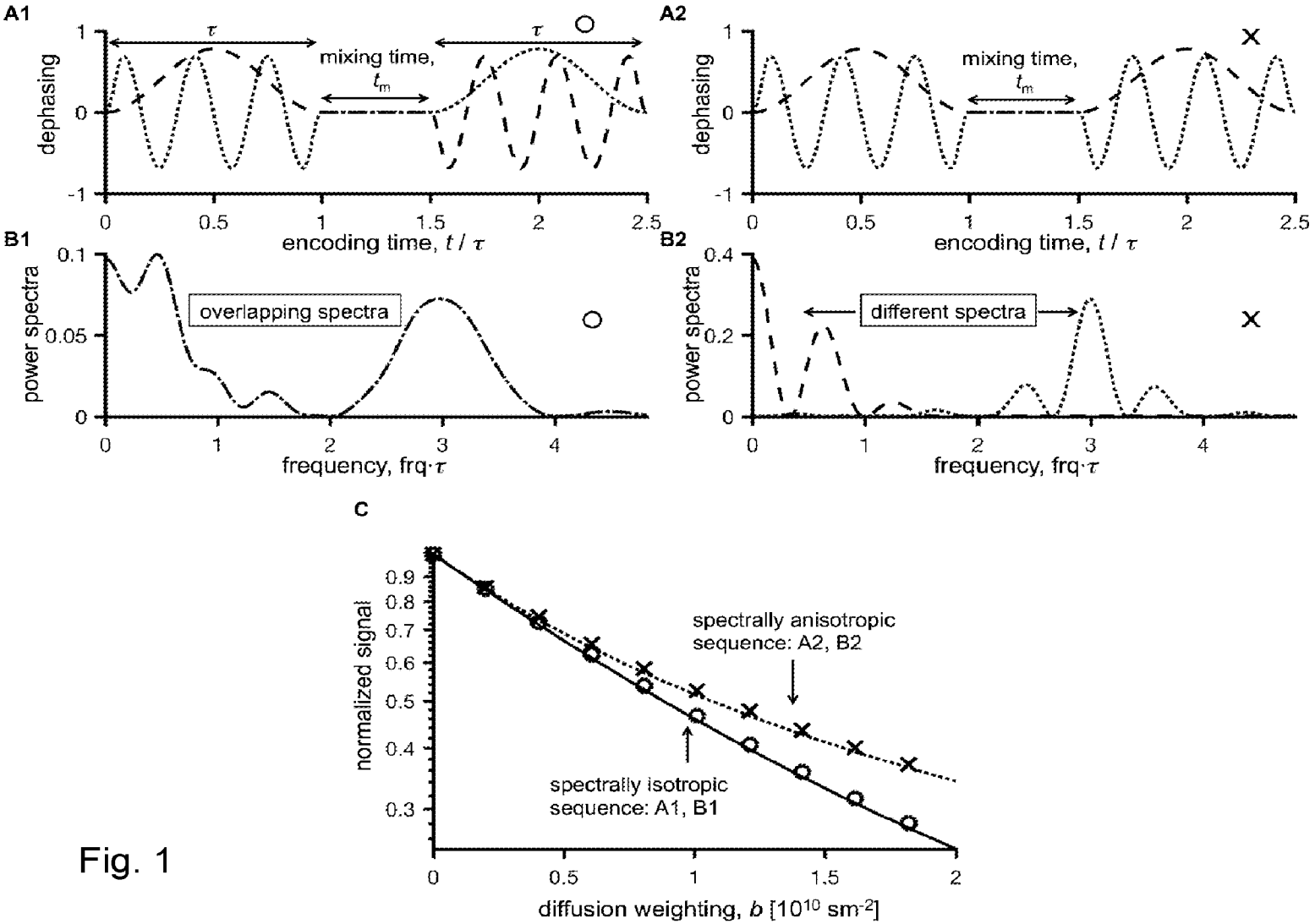
FIG. 1 illustrates dephasing waveforms and power spectra for two diffusion encoding sequences and simulations of corresponding attenuation curves.

To facilitate understanding of the present inventive concept, a discussion of some theoretical concepts will now be provided.

Theory

Considering an arbitrary effective gradient waveform g(t) during the diffusion encoding time $\tau$, the signal is given by the ensemble average $\langle \exp(i\gamma\int_0^\tau g(t)\,\Delta r(t)dt)\rangle$, where $\gamma$ is the nuclear gyromagnetic ratio and $\Delta r(t)$ is displacement. When multiple compartment systems are considered, the ensemble averaging takes place over sub-ensembles, compartments with different diffusion properties, e.g. pore size, shape and orientation. In the limit of low diffusion encoding gradients, the signal attenuation can be approximated by the second order cumulant expansion (6), corresponding to the Gaussian phase approximation (GPA).

For a single compartment or a sub-ensemble with a Gaussian diffusion process characterized by an apparent diffusion tensor D, for which displacement correlations are negligible during diffusion encoding, the signal attenuation is given by $E=\exp(-\beta)$, where $$\beta=\int_0^\tau F^T(t)DF(t)dt \text{ and} \tag{15}$$

F(t) is the temporal dephasing vector, $$F(t)=\gamma\int_0^t g(t')dt'. \tag{16}$$

where $\gamma$ is the nuclear gyromagnetic ratio and g(t) the waveform of the diffusion encoding gradient sequence.

The diffusion tensor D carries information about compartment anisotropy. The dephasing vector F(t) can be expressed as the Hadamard product of the amplitude q and the normalized waveform $\tilde{F}(t)$, $$F(t)=q\circ\tilde{F}(t). \tag{17}$$

For non-Gaussian diffusion and for the Gaussian approximation of the signal cumulant expansion (second order cumulant expansion), the attenuation is given by $$\beta=\int_{-\infty}^{\infty}F^T(\omega)D(\omega)F(-\infty)d\omega, \tag{18}$$

where $$F(\omega)=\int_0^\tau F(t)e^{-i\omega t}dt \tag{19}$$

and $D(\omega)$ is the diffusion spectrum, i.e. the spectrum of the velocity correlation tensor, $\chi(t)=\langle v^T(t)v(0)\rangle$. The frequency domain analysis can easily be applied to arbitrary gradient waveforms. Most importantly, it allows for an intuitive understanding of the restricted diffusion effects in 3D diffusion encoding, which can facilitate designing different encoding waveforms.

With Einstein summation convention (i.e. summing over repeated indices), we have $$\beta=\int_{-\infty}^{\infty}F_1(\omega)F_j(-\omega)D_{ij}(\omega)d\omega. \tag{20}$$

In the principal axis system of the compartment/confinement (PASC) (7), the diffusion spectrum is given by $D(\omega))=R\lambda(\omega)R^{-1}$, where $\lambda(\omega)$ is a diagonal matrix and are R is the rotation matrix. The dephasing spectra are given also as $$F(\omega)=q\circ\int_0^\tau\tilde{F}(t)e^{-i\omega t}dt=q\circ\tilde{F}(\omega). \tag{21}$$

To simplify notations, we define the integral operators $\widehat{F_iF_j}$; as $$\widehat{F_iF_{j*\lambda_k}}\equiv\int_{-\infty}^{\infty}F_1(\omega)\lambda_k(\omega)F_j^*(\omega)d\omega, \tag{22}$$

where i, j, k∈1, 2, 3 and the superscript * denotes complex conjugation. Note that $$\widehat{F_iF_i}=|\widehat{F_i}|^2 \text{ and } \widehat{F_iF_j}+\widehat{F_jF_i}=2\mathrm{Re}\{\widehat{F_iF_j}*\}.$$

By adopting the Einstein summation convention and using the definition in Eq. (22), Eq. (18) becomes $$\beta=R_{ki}R_{jk}\widehat{F_iF_i}*\lambda_k. \tag{23}$$

The attenuation (23) can be expressed in terms of the apparent diffusivities $$\Lambda_{ijk}\equiv\frac{\int_{-\infty}^{\infty}F_i(\omega)\lambda_k(\omega)F_j^*(\omega)d\omega}{\int_{-\infty}^{\infty}F_i(\omega)F_j^*(\omega)d\omega} \tag{24}$$

and the B tensor $$B_{ij}\equiv\int_{-\infty}^{\infty}F_1(\omega)F_j^*(\omega)d\omega \tag{25}$$

as $$\beta=\beta_{ij}R_{ki}R_{kj}\Lambda_{ijk}. \tag{26}$$

For Gaussian diffusion, i.e. time/frequency independent, $\Delta_{ijk}=\lambda_k$ and $$\beta=\beta_{ij}R_{ki}R_{kj}\lambda_k. \tag{27}$$

By denoting $D_{ij}=R_{ki}R_{kj}\lambda_k$, Eq. (27) can be rewritten as the inner product) $\langle\bullet,\bullet\rangle$ of tensors B and D, $$\beta=\langle B,D\rangle. \tag{28}$$

Different models for $\lambda_i(\omega)$ may be applied. At low frequencies, $\lambda_k(\omega)$ can be Taylor expanded as $$\lambda_k(\omega)=\sum_{n=0}^{\infty}\frac{1}{n!}\lambda_k^{(n)}(0)\omega^n, \tag{29}$$

where n is an integer and $\lambda_k^{(n)}(0)$ is the n-th derivative of $\lambda_k(\omega)$ at zero frequency. For restricted diffusion we have $$\lambda_i(\omega) = D_{i0}\sum_{k=1}^{\infty}\frac{a_{k,i}B_{k,i}\omega^2}{a_{k,i}^2D_i^2+\omega^2}. \tag{30}$$

In this case, the Eq. (29) can be written in terms of the even powers of ω and $\lambda_i^{(n)}(0)$ expressed in terms of restriction size (7).

Inserting Eq. (29) into Eq. (23) yields $$\beta = \sum_{n=0}^{\infty}\frac{1}{n!}M_{ij}^{(n)}R_{ki}R_{kj}\lambda_k^{(n)}(0), \tag{31}$$

where $$M_{ij}^{(n)} = \int_{-\infty}^{\infty}F_i(\omega)F_j^*(\omega)\omega^n d\omega \tag{32}$$

are the moments of the dephasing spectra represented as a tensor $M^{(n)}$, where $M_{ij}^{(n)}$ are the tensor elements. For Gaussian diffusion, only $B_{1j}=M_{ij}^{(0)}$ needs to be considered.

In terms of the normalized spectra $\tilde{F}(\omega)$, the tensor $M^{(n)}$ is given by $$M_{ij}^{(n)}=q_iq_j\int_{-\infty}^{\infty}\tilde{F}_i(\omega)\tilde{F}_j^*(\omega)\omega^n d\omega=Q_{ij}m_{ij}^{(n)}. \tag{33}$$

Spectral Content

The spectral content of a diffusion encoding sequence can be characterized in terms of the dephasing spectra or the normalized counterparts. The components of the normalized power spectra are given by:

$$S_{ij}(\omega)=\tilde{F}_i(\omega)\tilde{F}_j^*(\omega) \tag{34}$$

and the moments of the normalized power spectra are $$m_{ij}^{(n)} = \int_{-\infty}^{\infty}S_{ij}(\omega)|\omega|^n d\omega = \begin{cases} 0 \text{ if } M_{ij}^{(0)} = 0 \\ \dfrac{M_{ij}^{(n)}}{M_{ij}^{(0)}} \text{ if } M_{ij}^{(0)} > 0. \end{cases} \tag{35}$$

Note that $m_{ij}^{(0)}=0$ if $M_{ij}^{(0)}=0$ and $m_{ij}^{(0)}=1$ if $M_{ij}^{(0)}>0$. With $\mu_i^{(n)}$ we denote the eigenvalues of $m^{(n)}$.

The average encoding spectral content (for a single multidimensional encoding scheme) can be characterized by $$\langle\mu^{(n)}\rangle = \frac{\mu_1^{(n)}+\mu_2^{n)}+\mu_3^{(n)}}{\mu_1^{(0)}+\mu_2^{(0)}+\mu_3^{(0)}}, \tag{36}$$

where n is any positive real number, $n>0 \wedge n\in \mathbb{R}$. With brackets ⟨ . . . ⟩ we are denoting the averaging operation. The difference of $\langle\mu^{(n)}\rangle$ for any n>0 can be used to compare two encoding schemes. The value of the denominator in Eq. (36) provides a count of non-zero eigenvalues of the diffusion encoding tensor B.

Spectral Anisotropy

The spectral anisotropy of diffusion encoding (for a single multidimensional encoding scheme) can be quantified by comparing different eigenvalues of $m^{(n)}$, i.e. the values $\mu_i^{(n)}$. Any measure of tensor anisotropy, e.g. fractional anisotropy, can be applied to the tensors $m^{(n)}$. Note that the spectral anisotropy can only be defined for encoding schemes, which have more than one non-zero eigenvalues of the diffusion encoding tensor. To quantify spectral anisotropy (SA), the following equation, analogous to the fractional anisotropy, may be used:

$$SA^{(n)} = \left[\frac{1}{2}\frac{\left(\begin{array}{c}\mu_1^{(0)}\mu_2^{(0)}(\mu_1^{(n)}-\mu_2^{(n)})^2+\mu_2^{(0)}\mu_3^{(0)}(\mu_2^{(n)}-\mu_3^{(n)})^2+\\ \mu_3^{(0)}\mu_1^{(0)}(\mu_3^{(n)}-\mu_1^{(n)})^2\end{array}\right)}{\mu_1^{(n)^2}+\mu_2^{(n)^2}+\mu_3^{(n)^2}}\right]^{1/2}, \tag{37}$$

where n is any positive real number, $n>0 \wedge n\in \mathbb{R}$, which can be adjusted to control the sensitivity to spectral anisotropy. Note that $SA^{(n)}$ is always in the range 0-1.

Matching spectral content or "tuning" a multidimensional diffusion encoding scheme and a directional encoding scheme could be done numerically. The following procedure is useful when the multidimensional encoding gradient waveforms have been obtained based on some prior optimization. 1. For a range of rotations of the input waveforms (e.g. along x, y, z axis), compute the product $p=m_{11}^{(n)}m_{12}^{(n)}m_{33}^{(n)}$; the choice of n depends on the range of frequencies that one may chose to prioritize in the "tuning", i.e. matching spectral power; several moments may be computed. 2. Find the maximum value of p computed in the previous step to and the rotation R that yields the maximum value of p. 3. Transform the input waveforms using the rotation R. 4. For each of the transformed waveforms, compute the moment $m^{(n)}$ and select the waveform for which the moment $m^{(n)}$ is closest to the average moment (considering two or three waveforms and the corresponding moments). 5. Use the shape of the waveform selected in step 4 for the directional encoding.

Powder Average Signal

Let us define $\beta_n\equiv M_{ij}^{(n)}R_{ki}R_{kj}\lambda_k^{(n)}(0)=M_{ij}^{(n)}D_{ij}^{(n)}$ in Eq. (31), which can also be written as an inner product of the tensors $M_{(n)}$ and $D^{(n)}$, $$\beta_n=\langle M^{(n)},D^{(n)}\rangle, \tag{38}$$

where $[M^{(n)}]_{ij}=M_{ij}^{(n)}$ and $[D^{(n)}]_{ij}=R_{ki}R_{kj}\lambda_k^{(n)}(0)$. Up to the $2^{nd}$ order of $M^{(n)}$), the cumulant expansion of the powder (directional) average signal yields $$E = \left\langle\exp\left(-\sum_{n=0}^{\infty}\frac{1}{n!}\beta_n\right)\right\rangle \approx \exp\left(-\kappa_1+\frac{1}{2}\kappa_2\right), \tag{39}$$

where $$\kappa_1 = \sum_{n=0}^{\infty}\frac{1}{n!}\langle\beta_n\rangle \text{ and} \tag{40}$$

$$\kappa_2 = \left\langle\left(\sum_{n=0}^{\infty}\frac{1}{n!}\beta_n\right)^2\right\rangle - \left(\sum_{n=0}^{\infty}\frac{1}{n!}\langle\beta_n\rangle\right)^2. \tag{41}$$

Expressed with the inner product notation, $$\kappa_1 = \sum_{n=0}^{\infty}\frac{1}{n!} < M^{(n)}, \langle D^{(n)}\rangle > \tag{42}$$

and $$\kappa_2 = \sum_{i=0}^{\infty}\sum_{j=0}^{\infty}\frac{1}{i!j!}\langle \mathbb{M}^{(i,j)}, \mathbb{C}^{(i,j)}\rangle, \tag{43}$$

where $$[\mathbb{M}^{(i,j)}]_{klmn} \equiv M_{kl}^{(i)}M_{mn}^{(j)} \text{ and} \tag{44}$$

$$[\mathbb{C}^{(i,j)}]_{klmn} \equiv [\langle D_{kl}^{(i)}D_{mn}^{(j)}\rangle - \langle D_{kl}^{(i)}\rangle\langle D_{mn}^{(j)}\rangle] \tag{45}$$

The attenuation term (43) can be used to quantify the curvature of the signal decay curve, which is related to the diffusion kurtosis or the variance of the distribution of apparent diffusion coefficients. Note that the definitions (44) and (45) are invariant under a permutation of the indices i and j. Considering only terms with i=0 and 2 (approximation for restricted diffusion), we have (46)

$$\kappa_1 = \langle M^{(0)}, \langle D^{(0)}\rangle\rangle + \tfrac{1}{2}\langle M^{(2)}, \langle D^{(2)}\rangle\rangle \tag{46}$$

and $$\kappa_2 = \langle \mathbb{M}^{(0,0)}\mathbb{C}^{(0,0)}\rangle + 2\langle \mathbb{M}^{(0,2)}, \mathbb{C}^{(0,2)}\rangle + \langle \mathbb{M}^{(2,2)}, \mathbb{C}^{(2,2)}\rangle. \tag{47}$$

Note that $\mathbb{M}^{(0,0)}$ and $\mathbb{C}^{(0,0)}$ correspond to the Gaussian terms, cf. Eq. 3 and 6 in ref (10). If $D_{kl}^{(0)}$ and $D_{kl}^{(2)}$ are uncorrelated, i.e. when the diffusivity in tortuosity limit (at long time) is independent from its time variation (slope at low frequencies), $\mathbb{C}^{(0,2)}=0$.

Relation to the Effective Confinement Size: Case of Restricted Diffusion

The $2^{nd}$ expansion coefficient of the restricted diffusion spectrum in Eq. (29) is given by (7)

$$\lambda_i^{(2)}(0) = C_i r_i^4 \tag{48}$$

where $C_i$ is the geometry factor and $r_i$ is the size of restriction along the principal axis i. Let us define the effective confinement tensor $$[\rho^4]_{ij} \equiv R_{ki}R_{kj}C_k\gamma_k^4. \tag{49}$$

Eq. (46) then becomes $$\kappa_1 = \langle M^{(0)}, \langle D^{(0)}\rangle\rangle + \tfrac{1}{2}\langle M^{(2)}, \langle \rho^4\rangle\rangle. \tag{50}$$

If $\lambda_k^{(0)}(0)$ is independent of direction and equal to $D_0$, the first term above is given by ⅓ trace$(M^{(0)})D_0 = bD_0$. The $\kappa_2$ can be evaluated considering the following:

$$[\mathbb{C}^{(0,0)}]_{klmn} = [\langle D_{kl}^{(0)}D_{mn}^{(0)}\rangle - \langle D_{kl}^{(0)}\rangle\langle D_{mn}^{(0)}\rangle], \tag{51}$$

$$[\mathbb{C}^{(0,2)}]_{klmn} = [\langle D_{kl}^{(0)}\rho^4_{mn}\rangle - \langle D_{kl}^{(0)}\rangle\langle \rho^4_{mn}\rangle], \tag{52}$$

and $$[\mathbb{C}^{(2,2)}]_{klmn} = [\langle \rho^4_{kl}\rho^4_{mn}\rangle - \langle \rho^4_{kl}\rangle\langle \rho^4_{mn}\rangle], \tag{53}$$

If $D_{kl}^{(0)}$ and $D_{kl}^{(2)}$ are uncorrelated, $\mathbb{C}^{(0,2)}=0$ and $$\kappa_2 \langle \mathbb{M}^{(0,0)}, \mathbb{C}^{(0,0)}\rangle + \langle \mathbb{M}^{(2,2)}, \mathbb{C}^{(2,2)}\rangle. \tag{54}$$

Case of Isotropic Diffusion Weighting

Considering the definitions $[\mathbb{I}]_{kl} \equiv \delta_{kl}$ and $[\mathbb{I}_{iso}]_{klmn} \equiv \delta_{kl}\delta_{mn}$, we have $M^{(0)}=bI$, $M^{(2)}=q^2m^{(2)}$, $[\mathbb{M}^{(0,0)}]_{klmn}=b^2\delta_{kl}\delta_{mn}$, $[\mathbb{M}^{(0,2)}]_{klmn}=bq^2m_{kl}^{(2)}\delta_{mn}$ and $[\mathbb{M}^{(2,2)}]_{klmn} \equiv q^4m_{kl}^{(2)}m_{mn}^{(2)}$.

$$\kappa_1 = b\langle I, \langle D^{(0)}\rangle\rangle + \tfrac{1}{2}q^2\langle m^{(2)}, \langle \rho^4\rangle\rangle. \tag{55}$$

$$\kappa_2 = b^2\langle \mathbb{I}_{iso}, \mathbb{C}^{(0,0)}\mathbb{I}\rangle + bq^2\langle I\otimes m^{(2)}, \mathbb{C}^{(0,2)}\rangle + q^4\langle m^{(2)}\otimes m^{(2)}, \mathbb{C}^{(2,2)}\rangle, \tag{56}$$

where ⊗ denotes a tensor product. The first term in Eq. (56) arises from the variance of isotropic diffusivities, i.e. the variance of tensor traces, at zero frequency (long time regime), while the remaining terms represent a variance due to compartment size and anisotropy.

Case Isotropic Diffusion Weighting without Spectral Anisotropy

When the encoding is also spectrally isotropic, $m^{(2)}=m^{(2)}I$, $$\kappa_1 = b\langle I, \langle D^{(0)}\rangle\rangle + \tfrac{1}{2}q^2m^{(2)}\langle I, \langle \rho^4\rangle\rangle \text{ and} \tag{57}$$

$$\kappa_2 = b^2\langle \mathbb{I}_{iso}, \mathbb{C}^{(0,0)}\rangle + bq^2\langle \mathbb{I}_{iso}, \mathbb{C}^{(0,2)}\rangle + q^4m^{(2)}m^{(2)}\mathbb{I}\,\mathbb{C}_{iso}, \mathbb{C}^{(2,2)}. \tag{58}$$

Comparing Eqs. (56) and (58), we note that in the case of spectrally isotropic encoding, the additional variance due to compartment anisotropy is eliminated and only the variance due to compartment size remains. Changing spectral anisotropy could be used to isolate the time-dependent diffusion effects associated with anisotropic compartments.

Axial Symmetry:

Case of a Single Compartment

Here we adopt simplified notations $F=F(\omega)$ and $\lambda=\lambda(\omega)$. For axisymmetric diffusion encoding with dephasing spectra $F=(F_\perp, F_\parallel, F_\perp)$ and the diffusion spectra in the principle axis system of confinement/compartment (PASC), $$\lambda = \begin{pmatrix} \lambda_\perp & 0 & 0 \\ 0 & \lambda_\perp & 0 \\ 0 & 0 & \lambda_\parallel \end{pmatrix}, \tag{59}$$

the attenuation in Eq. (23) yields $$\beta = \frac{1}{3}(2\overline{F_\perp F_\perp^*} + \overline{F_\parallel F_\parallel^*})(2\lambda_\perp + \lambda_\parallel) + \frac{2}{3}(\overline{F_\parallel F_\parallel^*} - \overline{F_\perp F_\perp^*})(\lambda_\parallel + \lambda_\perp)P_2(\cos^2(\theta)) - \frac{1}{2}(\overline{F_\perp F_\parallel^*} + \overline{F_\parallel F_\perp^*})(\lambda_\parallel + \lambda_\perp)\sin(2\theta), \tag{60}$$

where $P_2(x)=(3x^2-1)/2$ is the second Legendre polynomial, $\pi/2\pm\theta$ is the angle between the main symmetry axes of the diffusion tensor and the diffusion encoding. By axially symmetric diffusion encoding we here strictly refer to the symmetry of $B=M^{(0)}$. For Gaussian (time/frequency independent) diffusion, the last term in Eq. (60), containing cross products of dephasing spectra, vanishes if $\int_{-\infty}^{\infty}F_\perp(\omega)F_\parallel(-\omega)d\omega=0$. According to the Plancherel's theorem, the above condition translates to $\int_0^\tau F_\perp(t)F_\parallel(t)dt=0$, which is fulfilled if the vector F(t) is always parallel to the right circular conical surface or the q-trajectory has at least a three-fold symmetry (3, 4) or simply when the product $F_\perp(t)F_\parallel(t)=0$ at all times. It is evident, that the last term in Eq. (60) vanishes for low compartment anisotropy. Numerical calculations, using the qMAS waveforms (2, 11), show that for largely anisotropic compartments, e.g. consisting of cylinders, this term is relatively small.

Without the cross product term, the expression (60) can be simplified $$\beta=\beta_{+}+\beta_{-}P_2(\cos^2(\vartheta)) \tag{61}$$

where $$\beta_{+}=\left(2\overline{|F_{\perp}|^2}+\overline{|F_{\|}|^2}\right)\frac{1}{3}(2\lambda_{\perp}+\lambda_{\|})=\frac{1}{3}[2b_{\perp}(2\Lambda_{\perp\perp}+\Lambda_{\perp\|})+b_{\|}(2\lambda_{\|\perp}+\Lambda_{\|\|})] \tag{62}$$

and $$\beta_{-}=\frac{2}{3}\left(\overline{F_{\|}^2}-\overline{F_{\perp}^2}\right)(\lambda_{|}-\lambda_{\perp})=\frac{2}{3}[b_{\|}(\Lambda_{\|\|}-\Lambda_{\|\perp})-b_{\perp}(\Lambda_{\perp\|}-\Lambda_{\perp\perp})]. \tag{63}$$

Here we use notations $$\Lambda_{ij}\equiv\frac{\int_{-\infty}^{\infty}F_i(\omega)\lambda_j(\omega)F_i^*(\omega)d\omega}{\int_{-\infty}^{\infty}F_i(\omega)F_i^*(\omega)d\omega} \tag{64}$$

and $$b_i\equiv\int_{-\infty}^{\infty}F_i(\omega)F_i^*(\omega)\,d\omega, \tag{65}$$

where $i, j\in\perp,\|$. $\wedge_{ij}$ is the apparent diffusion coefficient along axis j in PASC due to the diffusion encoding waveform i.

If all compartments in a sample are identical, the powder/directional average, $\langle e^{-\beta}\rangle$, is given by $$E=e^{-\beta_{+}}\frac{\sqrt{\pi}}{2}\frac{e^{A/3}}{\sqrt{A}}\operatorname{erf}(\sqrt{A}), \tag{66}$$

where $A=3/2\beta_{-}$. The isotropic diffusivity (D), which in the case of a single compartment corresponds to the mean diffusivity (MD), is given by $D=\beta_{+}/b$. Note that when the two waveforms have identical spectral content, i.e. $\tilde{F}_{\perp}(\omega)=\tilde{F}_{\|}(\omega)$, then $\beta_{+}=bD$ and $\beta_{-}=\frac{2}{3}\Delta b\Delta D$, where $b=b_{\|}+2b_{\perp}$, $D=(D_{\|}+2D_{\perp})/3$, $\Delta b=b_{\|}-b_{\perp}$ and $\Delta D=D_{\|}-D_{\perp}$. Thus, varying the shape of the diffusion encoding though $\Delta b$ allows quantifying diffusion anisotropy at zero frequency, $D^{(O)}$(4).

Compartment anisotropy brings about a dispersion of apparent diffusion coefficients, which will be affected also by the effects of time-dependent diffusion through $\beta_{-}$ in Eq. (63). The second central moment of the apparent diffusion distribution, due to compartment anisotropy, here denoted $V_A$ (2, 4), is given by $$V_A=\frac{4}{5}\left(\frac{A}{3b}\right)^2=\frac{4}{5}\left(\frac{\beta-}{2b}\right)^2, \tag{67}$$

where $$\beta=\frac{2}{3}\left(\hat{F}_{\|}^2-\hat{F}_{\perp}^2\right)(\lambda_{\|}-\lambda_{\perp})=\frac{2}{3}[b_{\|}(\Lambda_{\|\|}-\Lambda_{\|\perp})-b_{\perp}(\Lambda_{\perp\|}-\Lambda_{\perp\perp})]=\frac{1}{3}[2b_{\perp}(2\Lambda_{\perp\perp}+\Lambda_{\perp\|})+b_{\|}(2\Lambda_{\|\perp}+\Lambda_{\|\|})]. \tag{68}$$

The powder average signal is thus given by $$E\approx\exp(-bD+\tfrac{1}{2}b^2V_A+\mathcal{O}[b^3]). \tag{69}$$

For isotropic encoding with $b_{\|}=b_{\perp}=b/3$ we have $$\beta_{+}^{iso}=\frac{b}{9}[2(2\Lambda_{_\perp}+\Lambda_{\perp\|})+2\Lambda_{|\perp}+\Lambda_{|\|}],$$

$$\beta_{-}^{iso}=\frac{2b}{9}[\Lambda_{|\|}-\Lambda_{\perp\|}+\Lambda_{\perp\perp}-\lambda_{\|\perp}],$$

$$V_A^{iso}=\frac{4}{5\cdot 9^2}(\Lambda_{\|\|}-\Lambda_{\perp\|}+\Lambda_{\perp\perp}-\Lambda_{\|\perp})^2$$

and for directional encoding with $b_{\perp}=0$ and $b_{\|}=b$, we have $$\beta_{+}^{dir}=\frac{b}{3}(2\Lambda_{\|\perp}+A_{\|\|}),$$

$$\beta_{-}^{dir}=\frac{2b}{3}[\Lambda_{\|\|}-\Lambda_{\perp\|}]\text{ and}$$

$$V_A^{dir}\frac{4}{5\cdot 9}(\Lambda_{\|\|}-A_{\perp\|})^2.$$

For purely isotropic diffusion without dispersion of isotropic diffusivities, where $\lambda_{\|}=\lambda_{\perp}=\lambda_0$, we have $V_A=0$, $$\beta_{+}^{iso}=\frac{b}{3}(2\Lambda_{\perp 0}+\Lambda_{\|0})$$

and $\beta_{+}^{dir}=b\theta_{\|0}$. Note that $V_A>0$ only in the presence of anisotropic restrictions/compartments. Most importantly, $V_A^{iso}=0$ for anisotropic restrictions only when diffusion encoding is also spectrally isotropic, but $V_A^{iso}>0$ for spectrally anisotropic encoding. Varying spectral anisotropy may thus allow detecting time/frequency dependent diffusion effects in anisotropic compartments. On the other hand, the unbiased information about compartment anisotropy, i.e. not confounded by time/frequency dependent diffusion effects, can be obtained if the diffusion encoding waveforms with different shape of $B=M^{(O)}$ are spectrally tuned, i.e. have adequately similar mean spectral content. The different waveforms that are used to generate B, may also be self-tuned, i.e. have low spectral anisotropy.

Multiple Compartments

Consider powder-averaged signals from multiple compartments, each characterized with an apparent isotropic diffusivity D and an apparent diffusion variance due to shape anisotropy (anisotropic variance) $V_A$. By "apparent" we mean that the values depend on the anisotropy of B and temporal or spectral characteristics of the encoding waveforms. The total powder average signal is given by $$E\approx\langle\exp(-bD+\tfrac{1}{2}b^2V_A+\mathcal{O}[b^3])\rangle\approx\exp(-b\langle D\rangle+\tfrac{1}{2}b^2V+\mathcal{O}[b^3]), \tag{70}$$

where $$V=V_t+\langle V_A\rangle. \tag{71}$$

The total variance V is given by the sum of the isotropic variance $V_I=\langle D^2\rangle-\langle D\rangle^2$ and the average anisotropic variance $\langle V_A\rangle$. Note that the $V_I$ comprises size dispersion effects from both isotropic and anisotropic compartments. For isotropic encoding tensors B, which are also spectrally isotropic, $\langle V_A\rangle=0$. As we noted before, for spectrally anisotropic encoding with isotropic B, a residual variance is expected, so that $\langle V_A\rangle>0$.

Specific Sensitivity to Time/Frequency Dependent Diffusion in Anisotropic Compartments To illustrate how spectral anisotropy can provide specific sensitivity for detecting time/frequency dependent diffusion effects in anisotropic compartments, the higher order terms in Eq. (70), denoted with $\mathcal{O}[b^3]$, need to be considered. For the sake of argument, it should suffice to acknowledge that the higher order cumulants in the remainder $\mathcal{O}$ are not independent from the lower order cumulants.

Let us consider the difference in signal attenuation $\Delta \ln E$ from a directional and isotropic diffusion encoding, where all the waveforms have identical spectral content (tuned to each other and self-tuned, i.e. no spectral anisotropy). The attenuation difference is in this case given by $$\Delta \ln E=\tfrac{1}{2}b^2\langle V_A\rangle+\mathcal{O}[b^3,\langle D\rangle,V_1,\langle V_A\rangle], \tag{72}$$

where we have noted the dependence on the lower order cumulants in the remainder. In other words, the remainder entangles information about $\langle D\rangle$, $V_I$ and $\langle V_A\rangle$. Now, let's consider a similar pair of directional and isotropic encoding schemes, tuned to each other and spectrally isotropic, but with different timing parameters ($\tau$) compared to the first pair of encoding, i.e. with a different mean spectral content. We can now consider the difference between the attenuation differences for the first and the second encoding pair, $\Delta \ln E(\tau_2)-\Delta \ln E(\tau_1)$. Due to the remainder terms, the difference is modulated by the time dependence (time-dependent diffusion) in $\langle D\rangle$ and $V_I$. Thus the difference does not isolate the time/frequency dependent effects in the anisotropic compartment. To avoid this issue and completely isolate the time dependence (time-dependent diffusion) of anisotropic structures, we propose to vary spectral anisotropy.

Let us consider two isotropic encoding schemes with different degrees of spectral anisotropy, e.g. spectrally anisotropic and isotropic. The attenuation difference for these two encoding schemes is given by $$\Delta \ln E^{iso}=\frac{1}{2}b^2\langle \tilde{V}_A\rangle+O[b^3,\langle D\rangle,V_I,\langle O\tilde{V}_A\rangle] \tag{73}$$

where we used $$\langle \tilde{V}_A\rangle$$

to denote the residual variance due to spectral anisotropy. In this case we have not altered the mean spectral content but only the spectral anisotropy, which is expected to affect only the anisotropic compartments, thus only $$\langle \tilde{V}_A\rangle$$

is affected and not $\langle D\rangle$ or $V_I$. Consequently, also the remainder terms will only be affected by the time/frequency dependent diffusion effects in the anisotropic compartments.

EXAMPLE

FIG. 1 illustrates dephasing waveforms and power spectra for two diffusion encoding sequences and simulations of corresponding attenuation curves. Inset A1 shows scaled dephasing vector waveforms for a first diffusion encoding sequence, along two orthogonal directions (i.e. along the eigenvectors of the corresponding B tensor), dotted line and dashed line. Inset B1 shows the corresponding power spectra for the waveforms. Inset A2 shows scaled dephasing vector waveforms for a second diffusion encoding sequence, along two orthogonal directions (i.e. along the eigenvectors of the corresponding B tensor), dotted line and dashed line. Inset B1 shows the corresponding power spectra for the waveforms.

The first diffusion encoding sequence is in-plane spectrally isotropic (SA=0). This may be seen from the overlapping power spectra in inset B1. The second diffusion encoding sequence is in-plane spectrally anisotropic (SA=0.68). In inset B2 the power spectra are non-overlapping. The first and the second diffusion sequences are however spectrally tuned. Both schemes yield identical B tensors as well as traces of the $m^{(2)}$ tensors.

Inset C shows the normalized signal attenuation at $\tau$=95 ms. The solid and dashed lines are from calculations with the spectrally isotropic waveforms (A1, B1) and spectrally anisotropic waveforms (A2, B2), respectively. The markers show results of Monte Carlo simulations for the spectrally isotropic waveforms (circles, A1, B1) and for the spectrally anisotropic waveforms (crosses, A2, B2). The signal attenuation difference is observed only for time-dependent anisotropic diffusion and not for time-dependent isotropic diffusion.

Powder averaging in the calculation was applied upon 1000 uniformly distributed rotations. The diffusion spectrum for restricted diffusion in an axially symmetric ellipsoidal pore was approximated using $D(\omega)$ for spherical geometry with radii of 1 μm along two axes and 5 μm along one axis. The intrinsic diffusivity $D_0=10^{-9}$ $m^2/s$ was used. The encoding time $t_e=2\tau+t_m$ was logarithmically spaced in the range 0.05-625 ms. The mixing time was adjusted to $t_m=0.2\ t_e$. In addition, Monte Carlo simulations where performed with the same geometry and intrinsic diffusivity using $5\cdot10^5$ walkers and time-steps. Powder averaging in the simulation was applied with 24 rotations with 10 linearly spaced diffusion weighting steps in the range $b=0\text{-}18\cdot10^9$ $s/m^2$.

Figure 2:
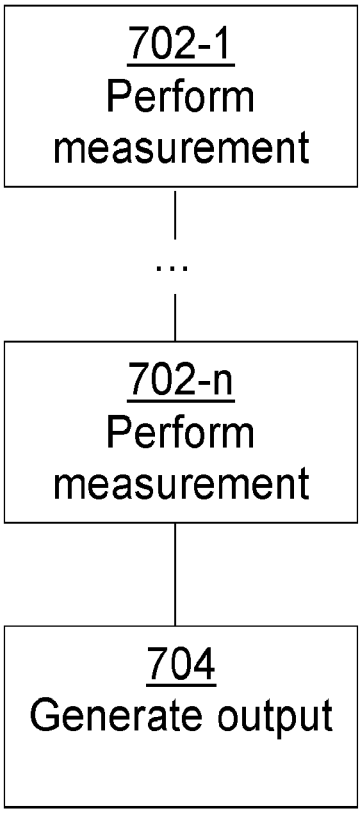
FIG. 2 illustrates a flow chart of a method of performing diffusion weighted magnetic resonance measurements on a sample.

The results show that effects of time-dependent diffusion in general multidimensional diffusion encoding (MDE) experiments can be analyzed in the frequency domain. The m or M tensors (which may be referred to as dephasing moment tensors) provide additional characterization of encoding waveforms in terms of their spectral content. While the B tensor provides sensitivity to the long-time or Gaussian diffusivity, the dephasing moment tensors provide sensitivity to time-dependent diffusion. While varying anisotropy of the B tensor gives contrast specific to the long-time diffusion anisotropy, varying spectral anisotropy yields contrast specific to time-dependent diffusion anisotropy. In the present example with planar diffusion encoding, the spectral anisotropy can be varied independently from the mean spectral content. The resulting signal attenuation difference carries highly specific information, isolating time-dependent diffusion in anisotropic domains Description of Embodiments FIG. 2 illustrates a general flow chart of a method of performing diffusion weighted magnetic resonance measurements on a sample. The sample may for example be a biological sample including water, such as brain tissue or biopsy samples of (suspensions) of any organs cell. The method however has a more general applicability and may be used for analyzing also other types of samples, such as rocks. More generally, the sample includes a nuclear spin system whose properties may be measured by nuclear magnetic resonance techniques.

To facilitate understanding of the method, reference will in the following be made to the attenuated echo signal from a single voxel, i.e. a single spatial channel (in the case of an MRI method) or a single frequency channel (in the case of NMR method). As is well-known in the art, this resolution may be achieved by applying a further magnetic gradient to the sample during the encoding sequence (e.g. an imaging gradient in the case of an MRI method). To identify/isolate the echo signal component from the partial volume of the sample corresponding to the voxel, the measurement signals from the sample may be subjected to a Fast Fourier Transform as is well-known in the art, thereby transforming the spectral components of each echo signal from the sample into a plurality of spatial or frequency regions of the sample.

As is well-known in the art the spatial resolution of an NMR spectrometer or MRI device is limited by inter alia the strength of the magnetic field, the magnitude of the gradient pulse sequence applied to the sample and the slew rate. Accordingly, an echo signal for a voxel will typically include contributions from a plurality microscopic compartments within the partial volume of the sample corresponding to the voxel.

The method may be performed using a state-of-the-art NMR spectrometer or MRI device. As is well-known in the art, such devices may include a controller for controlling the operation of the device, inter alia the generation of the magnetic gradient pulse sequences, the acquisition of signals as well as sampling and digitizing the acquired signals for forming data representing the acquired signals (i.e. the measured signals). The controller may be implemented on one or more processors of the MRI device wherein the generation of the relaxation encoding sequences and the magnetic gradient pulse sequences may be implemented using software instructions which may be stored on a computer readable media (e.g. on a non-transitory computer readable storage medium) and be executed by the one or more processors of the device. The software instructions may for example be stored in a program/control section of a memory of the device, to which the one or more processors of the device has access. It is however also possible that, instead of using software instructions, the controller method may be implemented in the form of dedicated circuitry of the device/computer such as in one or more integrated circuits, in one or more application-specific integrated circuits (ASICs) or field-programmable gate arrays (FPGAs), to name a few examples.

Data representing the acquired signals may be stored in a data memory of the device, or of a computer or the like which may be connected to the device.

Data processing may be performed by a processing device. The operations may be implemented in a set of software instructions which may be stored or embodied on a non-transitory computer readable media and be executed by the processing device. For instance, the software instructions may be stored in a program/control section of a memory of the NMR spectrometer/MRI device and executed by one or more processor units of the spectrometer/device. However, it is equally possible to carry out the calculations on a device which is separate from the NMR spectrometer or MRI device, for example on a computer. The device and the computer may for example be arranged to communicate via a communication network such as a LAN/WLAN or via some other serial or parallel communication interface. It should further be noted that, instead of using software instructions, the data processing may be implemented in a processing device in the form of dedicated circuitry of the device/computer such as in one or more integrated circuits, in one or more ASICS or FPGAs, to name a few examples.

With reference to FIG. 2, the method comprises performing diffusion weighted magnetic resonance measurements on the sample (step 702-1 through 702-n). The NMR/MRI device may generate diffusion encoding sequences and acquire the resulting signal attenuations. Each measurement may include an encoding block, followed by a detection block. The encoding block may include an RF-sequence and a diffusion encoding magnetic gradient sequence. For the purpose of acquiring echo signals, each diffusion encoding magnetic gradient pulse sequence may be supplemented with one or imaging magnetic gradients and optionally magnetic gradient correction gradients, as is well-known in the art.

Figure 3:
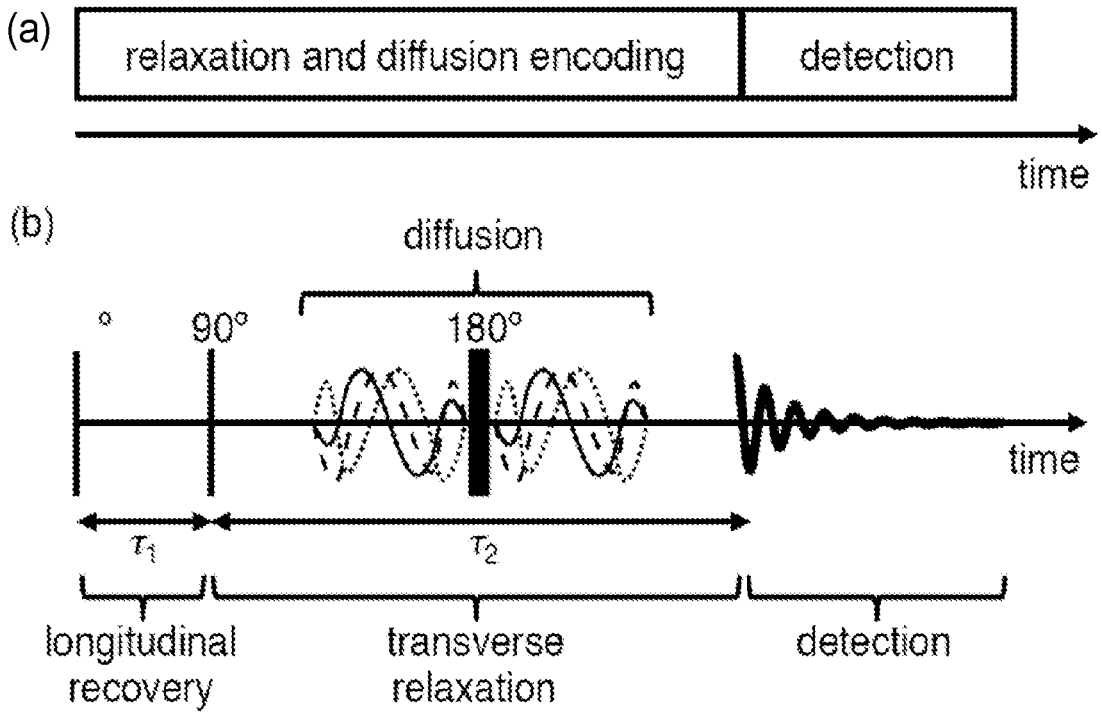
FIGS. 3a and 3b illustrate examples of pulse sequences.

An example of a pulse sequence comprising a block with relaxation and diffusion encoding preceding a block with signal detection is illustrated in FIG. 3a and a specific implementation in FIG. 3b. Accordingly, FIG. 3a shows an encoding block which modulates the echo signal according to the values of the relaxation rates and the diffusion encoding magnetic gradient sequence, and a detection block where the echo signal is read out (e.g. as a spectrum or an image). FIG. 3b illustrates a pulse sequence with 90° and 180° RF pulses (narrow and broad vertical lines), modulated gradients in three orthogonal directions (solid, dashed, and dotted lines), and detected signal (thick solid line). The signal is modulated by longitudinal recovery, transverse relaxation, and diffusion.

Starting from an initial state with complex transverse magnetization mxy equal to zero, the first 90° RF pulse flips the longitudinal magnetization mz into the transverse plane. During the time-delay with duration $\tau_1$, the longitudinal magnetization recovers towards the thermal equilibrium value $m_0$ with the longitudinal relaxation rate R1 . The second 90° pulse flips the recovered magnetization into the transverse plane where it decays towards zero with the transverse relaxation rate R1 for a time period $\tau_2$ before it is detected. During the $\tau_2$ period, a time-dependent magnetic field gradient is applied.

Generally, both spin echo encodings and stimulated echo encodings may be used. In either case the RF signal sequence may encode for attenuation due to only longitudinal, only transverse relaxation or both longitudinal and transverse relaxation. One example sequence may include a single 90° pulse and a single 180° pulse. The timing of the gradient pulse sequence in relation to the 180° pulse may be varied. For instance the gradient pulse sequence may be performed prior to or subsequent to the 180° pulse. Several such sequences may be repeated before acquisition/detection. Examples of stimulated echo sequences may include a first 90° pulse, a second 90° pulse and a third 90° pulse. The gradient pulse sequence may be performed between the first and the second 90° pulses, and/or subsequent to the third 90° pulse (i.e. before the detection block). These examples sequences are however merely provided as illustrative examples and other sequences are also possible. Preferably, a same RF signal sequence is used in all of the plurality of measurements, i.e. of all measurements of the first, the second and the third set.

The method may comprise performing a first measurement 702-1 with a first diffusion encoding sequence having a first diffusion weighting tensor representation $B_1$ with at least two non-zero eigenvalues. The method may comprise performing a second measurement 702-2 with a second diffusion encoding sequence having a second diffusion weighting tensor representation $B_2$ with at least two non-zero eigenvalues. The first tensor representation $B_1$ and the second tensor representation $B_2$ may have a same number of non-zero eigenvalues. Moreover, the eigenvalues of the first tensor representation $B_1$ may match the eigenvalues of the second tensor representation $B_2$ (for instance differ by 10% or less, or even be equal, at least substantially equal such as differ by 1% or less). Moreover, the first and the second diffusion encoding sequences may be configured to present a matching average spectral content, and to present a different degree of spectral anisotropy, as defined in the above.

An example of two such diffusion encoding sequences is shown in FIG. 1. In FIG. 1 the sequences are planar encoding sequences. i.e. having tensor representations with exactly two non-zero eigenvalues. It is however also possible to generate 3D diffusion encoding sequences, i.e. having tensor representations with exactly three non-zero eigenvalues. Diffusion encoding sequences may be designed using the above described numerical approach. Additionally or alternatively, diffusion encoding sequences may be designed employing the test cases described above. An iterative approach may be applied where, in case the test cases are not met with an initial design of the diffusion encoding sequences, one or more parameters of one or more of the diffusion encoding sequences may be altered. A new test may then be performed using the modified diffusion encoding sequences. Iterations may be performed until the test cases are met. For the purpose of the testing, the b-value of the first and second diffusion encoding sequence may be any single value in the range of $1*10^9$-$4*10^9$ s/m$^2$. Although, the test case as set out above refers to spherical compartments and cylindrical compartments of a 5 μm diameter it is also possible to use another diameter such as anywhere in the range of 5-15 μm. Compartment diameters in this range would also allow testing whether two diffusion encoding sequences meet the requirements of spectral matching and different degrees of spectral anisotropy.

The detection block of each measurement may include detecting the echo signal following the encoding block. The signal resulting from the plurality of measurements may be acquired and recorded as data. The echo signal may be sampled and digitized to form the data. The data may be stored for further data processing. The data may for instance be stored in a data memory of the device, or of a computer or the like which may be connected to the device.

The measurements may be powder averaged wherein each of the first and the second measurement may be repeated for a number of different measurement directions, preferably a plurality of directions. A first average signal attenuation may be calculated as an average of the signal attenuations resulting from the application of the first diffusion encoding sequence, for each measurement direction. Correspondingly a second average signal attenuation may be calculated as an average of the signal attenuations resulting from the application of the second diffusion encoding sequence, for each measurement direction.

In step 704 of the method, the processing device may generate an output based on the measured first (optionally averaged) and second (optionally averaged) signal attenuations resulting from the magnetic resonance measurements 702-1 and 702-2. The output may for instance be based on a difference between the first and second signal attenuations or a ratio of the first and second signal attenuations. The processing device may generate a corresponding output based on signal attenuations measured for each one of a plurality of voxels within a region of interest of the sample. The processing device may generate an output in the form of a digital image including an indication of voxels for which a signal attenuation acquired in the first measurement differs from a signal attenuation acquired in the second measurement by more than a threshold value. For instance, voxels where the first measurement differs from a signal attenuation acquired in the second measurement may be highlighted with an increased brightness, a deviating color, a bounding box and/or some other graphical element.

Although in the above, reference is made to a first and a second measurement with a first and a second diffusion encoding sequence, respectively, it should be noted that the method may include further measurements, such as a third measurement with a third diffusion encoding sequence. The third diffusion encoding sequence may have a second diffusion weighting tensor representation $B_3$ with at least two non-zero eigenvalues. The tensor representation $B_3$ may have a same number of non-zero eigenvalues as the tensor representations $B_1$ and $B_2$. Moreover, the eigenvalues of the third tensor representation $B_3$ may match the eigenvalues of the tensor representations $B_1$ and $B_2$. Moreover, the third diffusion encoding sequences may be configured to present an average spectral content matching the average spectral content of the first diffusion encoding sequence and the average spectral content of the second diffusion encoding sequence, and to present a degree of spectral anisotropy which differs from the degree of spectral anisotropy of the first diffusion encoding sequences and from the degree of spectral anisotropy of the second diffusion encoding sequences.

With reference to FIG. 2, step 702-1 of the method may alternatively include performing a first set of measurement performed with diffusion encoding sequences with different diffusion encoding strengths (b-values) and matching average spectral content and matching degree of spectral anisotropy. Correspondingly. step 702-2 may include performing a second set of measurement performed with diffusion encoding sequences with different diffusion encoding strengths and matching average spectral content and matching degree of spectral anisotropy. The diffusion encoding sequences of each one of the first set and the second set may have a respective tensor representation, the number of non-zero eigenvalues of the tensor representations for the respective diffusion encoding sequences of the first and second set being equal.

The detection block may include acquisition of a first set of signal attenuations and recording of a first data set representing the first set of acquired signal attenuations. The detection block may correspondingly include acquisition of a second set of signal attenuations and recording of a second data set representing the second set of acquired signal attenuations. Optionally, each measurement of each set may be powder averaged in a corresponding manner as set out above.

In step 704 of the method, the processing device may accordingly fit a function to the first data set representing the first set of (optionally averaged) signal attenuations to estimate a first signal attenuation curve E(b). The processing device may further fit the function to the second data set representing the second set of (optionally averaged) signal attenuations to estimate a second signal attenuation curve E(b). Any fitting function including the parameters relating to the components of the diffusion spectrum $D(\omega)$ or the eigen-modes $\lambda_i(\omega)$ or $\lambda_k^{(n)}(0)$, i.e. the n-th derivative of $\lambda_k(\omega)$ at zero frequency (Eq. 40) or the effective confinement tensor $\rho^4$ (Eqs. 52-56). The processing device may accordingly generate an output based on at least one parameter of the first fitting and the second fitting. Analogous to the above the processing device may generate a corresponding output based on signal attenuations measured for each one of a plurality of voxels within a region of interest of the sample.

In the above the inventive concept has mainly been described with reference to a limited number of examples. However, as is readily appreciated by a person skilled in the art, other examples than the ones disclosed above are equally possible within the scope of the inventive concept, as defined by the appended claims.

LIST OF REFERENCES

In the above disclosure, one or more numbers in parentheses or brackets refer to a correspondingly numbered reference document in the following list of references:

1. Westin C-F, Szczepankiewicz F. Pasternak O, et al.: Measurement Tensors in Diffusion MRI: Generalizing the Concept of Diffusion Encoding. Med Image Comput Comput Interv 2014; 17:209-216.
2. Lasič S, Szczepankiewicz F, Eriksson S, Nilsson M, Topgaard D: Microanisotropy imaging: quantification of microscopic diffusion anisotropy and orientational order parameter by diffusion MRI with magic-angle spinning of the q-vector. Front Phys 2014; 2:1-14.
3. Eriksson S, Lasič S, Topgaard D: Isotropic diffusion weighting in PGSE NMR by magic-angle spinning of the q-vector. J Magn Reson 2013; 226:13-8.
4. Eriksson S, Lasič S, Nilsson M, Westin C-F, Topgaard D: NMR diffusion-encoding with axial symmetry and variable anisotropy: Distinguishing between prolate and oblate microscopic diffusion tensors with unknown orientation distribution. J Chem Phys 2015; 142:104201.
5. Szczepankiewicz F, Lasič S, van Westen D, et al.: Quantification of microscopic diffusion anisotropy disentangles effects of orientation dispersion from microstructure: applications in healthy volunteers and in brain tumors. Neuroimage 2015; 104:241-52.
6. Stepršnik J: Validity limits of Gaussian approximation in cumulant expansion for diffusion attenuation of spin echo. Phys B 1999; 270:110-117.
7. Stepršnik J: Time-dependent self-diffusion by NMR spin-echo. Phys B 1993; 183:343-350.

The invention claimed is:

1. A method of performing diffusion weighted magnetic resonance measurements on a sample, the method comprising:

performing diffusion weighted magnetic resonance measurements on the sample, wherein said measurements includes:

a first measurement with a first diffusion encoding sequence having a first diffusion weighting tensor representation $B_1$ with at least two non-zero eigenvalues, a second measurement with a second diffusion encoding sequence having a second diffusion weighting tensor representation $B_2$ with at least two non-zero eigenvalues, wherein the first tensor representation $B_1$ and the second tensor representation $B_2$have a same number of non-zero eigenvalues, the eigenvalues of the first tensor representation $B_1$ matching the eigenvalues of the second tensor representation $B_2$, and wherein the first and the second diffusion encoding sequences are configured to present a matching average spectral content, and to present a different degree of spectral anisotropy.

2. A method according to claim 1, wherein the first and the second diffusion encoding sequences are configured such that had:

a third diffusion encoding sequence, having a normalized dephasing vector representation $F_3$ matching a first normalized dephasing vector representation $F_1$ of the first diffusion encoding sequence and having a non-zero diffusion encoding strength, been applied to a first test sample consisting of a collection of spherical compartments of a 5 μm diameter, and a fourth diffusion encoding sequence, having a normalized dephasing vector representation $F_4$ matching a second normalized dephasing vector representation $F_2$ of the second diffusion encoding sequence and having said non-zero diffusion encoding strength, been applied to said first test sample, a signal attenuation resulting from the third diffusion encoding sequence would match a signal attenuation resulting from the fourth diffusion encoding sequence;

and such that had:

the third diffusion encoding sequence been applied to a second test sample consisting of a collection of cylindrical compartments of a 5 μm diameter with a uniform orientation dispersion, and the fourth diffusion encoding sequence been applied to said second test sample, a signal attenuation resulting from the third diffusion encoding sequence would differ from a signal attenuation resulting from the fourth diffusion encoding sequence.

3. A method according to claim 1, wherein said first measurement includes acquiring a first signal attenuation, and said second of measurement includes acquiring a second signal attenuation.

4. A method according to claim 1, wherein said measurements include:

a first set of measurements including said first measurement and a plurality of additional measurements performed with said first diffusion encoding sequence applied to the sample with different rotations with respect to a measurement frame of reference, a second set of measurements including said second measurement and a plurality of additional measurements performed with said second diffusion encoding sequence applied to the sample with different rotations with respect to the measurement frame of reference.

5. A method according to claim 4, wherein:

each measurement of said first set of measurements includes acquiring a respective signal attenuation and the method comprises determining a first average signal attenuation based on said respective signal attenuations, and each measurement of said second set of measurements includes acquiring a respective signal attenuation and the method comprises determining a second average signal attenuation based on said respective signal attenuations.

6. A method according to claim 1, further comprising:

generating an output indicative of a difference between first and second signal attenuations or between first and second average signal attenuations.

7. A method according to claim 1, wherein said first tensor representation has three matching non-zero eigenvalues.

8. A method according to claim 1, wherein said second tensor representation has three matching non-zero eigenvalues.

9. A method according to claim 1, wherein performing said measurements includes, measuring a respective signal attenuation resulting from each one of said measurements, from each one of a plurality of voxels within a region of interest of the sample.

10. A method according to claim 1, further comprising generating an output including an indication of voxels for which a signal attenuation acquired in the first measurement differs from a signal attenuation acquired in the second measurement.

11. A method of performing diffusion weighted magnetic resonance measurements on a sample, the method comprising:

performing diffusion weighted magnetic resonance measurements on the sample, wherein said measurements includes:

a first set of measurement performed with diffusion encoding sequences with different diffusion encoding strengths and matching average spectral content and matching degree of spectral anisotropy, a second set of measurement performed with diffusion encoding sequences with different diffusion encoding strengths and matching average spectral content and matching degree of spectral anisotropy, wherein the degree of spectral anisotropy of the diffusion encoding sequences of the first set differs from the degree of spectral anisotropy of the diffusion encoding sequences of the second set.

12. A method according to claim 11, further comprising:

fitting a first function to a first data set representing said first set of measurements to estimate a first signal attenuation curve, and fitting a second function to a second data set representing said second set of measurements to estimate a second signal attenuation curve.

13. A method according to claim 12, further comprising generating an output based on at least one parameter of the first function and at least one parameter of the second function.

14. A method according to claim 11, wherein the diffusion encoding sequences of each one of the first set and the second set have a respective tensor representation, wherein a number of non-zero eigenvalues of the tensor representations are equal.

15. A method according to claim 11, wherein the average spectral content of each of the diffusion encoding sequences of the first set matches the average spectral content of each of the diffusion encoding sequences of the second set.

*16. A method of performing diffusion weighted magnetic resonance measurements on a sample comprising partial volumes having different diffusion characteristics, and extracting information relating to the different diffusion characteristics and microscopic structures of the sample, the method comprising:*

*performing on the sample a first diffusion weighted magnetic resonance measurement with a first diffusion encoding sequence having a first diffusion weighting tensor representation $B_1$ with at least two non-zero eigenvalues, and acquiring a first signal attenuation,*

*performing on the sample a second diffusion weighted magnetic resonance measurement with a second diffusion encoding sequence having a second diffusion weighting tensor representation $B_2$ with at least two non-zero eigenvalues, and acquiring a second signal attenuation,*

*wherein the first tensor representation $B_1$ and the second tensor representation $B_2$ have a same number of non-zero eigenvalues;*

*wherein for the first diffusion encoding sequence,*

$$\langle \mu^{(n)} \rangle = \frac{\mu_1^{(n)} + \mu_2^{(n)} + \mu_3^{(n)}}{\mu_1^{(0)} + \mu_2^{(0)} + \mu_3^{(0)}}, \text{ and}$$

$$SA^{(n)} = \left[ \frac{1}{2} \frac{\mu_1^{(0)}\mu_2^{(0)}(\mu_1^{(n)} - \mu_2^{(n)})^2 + \mu_2^{(0)}\mu_3^{(0)}(\mu_2^{(n)} - \mu_3^{(n)})^2 + \mu_3^{(0)}\mu_1^{(0)}(\mu_3^{(n)} - \mu_1^{(n)})^2}{\mu_1^{(n)2} + \mu_2^{(n)2} + \mu_3^{(n)2}} \right]^{1/2}$$

*where n is a positive real number and $\mu_i^{(n)}$ denotes eigenvalues of a tensor $m^{(n)}$ with elements*

$$m_{ij}^{(n)} = \int_{-\infty}^{\infty} \tilde{F}_i(\omega)\tilde{F}_j^*(\omega)|\omega|^n d\omega,$$

*where $\tilde{F}_i(\omega)$ and $\tilde{F}_j^*(\omega)$ are $i^{th}$ and $j^{th}$ components of a normalized dephasing vector, respectively, of a normalized dephasing spectrum $\tilde{F}(\omega)$ representation of the first diffusion encoding sequence, and*

*for the second diffusion encoding sequence,*

$$\langle \mu^{(n)} \rangle = \frac{\mu_1^{(n)} + \mu_2^{(n)} + \mu_3^{(n)}}{\mu_1^{(0)} + \mu_2^{(0)} + \mu_3^{(0)}}, \text{ and}$$

$$SA^{(n)} = \left[ \frac{1}{2} \frac{\mu_1^{(0)}\mu_2^{(0)}(\mu_1^{(n)} - \mu_2^{(n)})^2 + \mu_2^{(0)}\mu_3^{(0)}(\mu_2^{(n)} - \mu_3^{(n)})^2 + \mu_3^{(0)}\mu_1^{(0)}(\mu_3^{(n)} - \mu_1^{(n)})^2}{\mu_1^{(n)2} + \mu_2^{(n)2} + \mu_3^{(n)2}} \right]^{1/2}$$

*where n is a positive real number and $\mu_i^{(n)}$ denotes eigenvalues of a tensor $m^{(n)}$ with elements*

$$m_{ij}^{(n)} = \int_{-\infty}^{\infty} \tilde{F}_i(\omega)\tilde{F}_j^*(\omega)|\omega|^n d\omega,$$

*where $\tilde{F}_i(\omega)$ and $\tilde{F}_j^*(\omega)$ are $i^{th}$ and $j^{th}$ eigenvector, respectively, of a normalized dephasing spectrum $\tilde{F}(\omega)$ representation of the second diffusion encoding sequence;*

*wherein the first and the second diffusion encoding sequences are configured to:*

*present a matching average spectral content in a sense that the $\langle \mu^{(n)} \rangle$ calculated for the first diffusion encoding sequence matches the $\langle \mu^{(n)} \rangle$ calculated for the second diffusion encoding sequence, and*

*to present a different degree of spectral anisotropy in a sense that the $SA^{(n)}$ calculated for the first diffusion encoding sequence differs from the $SA^{(n)}$ calculated for the second diffusion encoding sequence; and*

*generating an output indicative of a difference between the first and second signal attenuations.*

* * * * *